US012580083B1

(12) United States Patent
Gulati et al.

(10) Patent No.: US 12,580,083 B1
(45) Date of Patent: Mar. 17, 2026

(54) PREDICTION OF PROBABILITY OF BODILY INJURY BASED ON VEHICLE DAMAGE

(71) Applicant: Mitchell International, Inc., San Diego, CA (US)

(72) Inventors: Abhijeet Gulati, San Diego, CA (US); Christopher Williamson, San Diego, CA (US); Joseph Hyland, San Diego, CA (US)

(73) Assignee: Mitchell International, Inc., San Diego, CA (US)

( * ) Notice: Subject to any disclaimer, the term of this patent is extended or adjusted under 35 U.S.C. 154(b) by 0 days.

(21) Appl. No.: 18/887,673

(22) Filed: Sep. 17, 2024

(51) Int. Cl.
*G06Q 40/00* (2023.01)
*G06Q 10/0635* (2023.01)
*G16H 50/30* (2018.01)

(52) U.S. Cl.
CPC ......... *G16H 50/30* (2018.01); *G06Q 10/0635* (2013.01)

(58) Field of Classification Search
CPC .......................... G16H 50/30; G06Q 10/0635
See application file for complete search history.

(56) References Cited

U.S. PATENT DOCUMENTS

| | | | | |
|---|---|---|---|---|
| 9,652,748 | B1 * | 5/2017 | Sanchez | ............. G06Q 10/1093 |
| 12,420,777 | B1 * | 9/2025 | Nave | ................... B60W 50/14 |
| 2016/0358129 | A1 * | 12/2016 | Walton | ................... G06Q 40/08 |
| 2018/0075538 | A1 * | 3/2018 | Konrardy | ............... G08G 1/005 |
| 2019/0318265 | A1 * | 10/2019 | Gould | ........................ G06F 8/65 |
| 2021/0398088 | A1 * | 12/2021 | Leise | .............. G06Q 10/08355 |
| 2021/0407687 | A1 * | 12/2021 | Pasch | ...................... A61B 5/747 |
| 2022/0067410 | A1 * | 3/2022 | Raz | ...................... A61B 5/7264 |
| 2022/0118931 | A1 * | 4/2022 | Qi | ..................... B60R 21/01338 |
| 2024/0370609 | A1 * | 11/2024 | Khademinejad | ........ G06F 30/20 |

FOREIGN PATENT DOCUMENTS

EP          4456041 A1 * 10/2024   ............. G08G 1/166

OTHER PUBLICATIONS

Golman et al: "Injury prediction in a side impact crash using human body model simulation", Accident Analysis and Prevention vol. 64, Mar. 2014, pp. 1-8 (Year: 2014).*

* cited by examiner

*Primary Examiner* — Edward J Baird
(74) *Attorney, Agent, or Firm* — Sheridan Ross P.C.

(57) ABSTRACT

A computer-implemented method comprises providing images and attributes of a damaged vehicle that has been damaged in a collision event to a trained computer vision machine learning model, which in response provides indicators of physical damage sustained by the damaged vehicle during the collision event; providing the indicators to a trained classifier machine learning model, which in response provides a predicted likelihood that bodily injury was sustained by an occupant of the damaged vehicle during the collision event and a confidence indicator representing a level of confidence that the predicted likelihood that bodily injury was sustained is correct; and providing the predicted likelihood of bodily injury and the confidence indicator to an analyst for use in evaluating a bodily injury claim related to the occupant of the damaged vehicle and the collision event.

21 Claims, 11 Drawing Sheets

Figure 2:
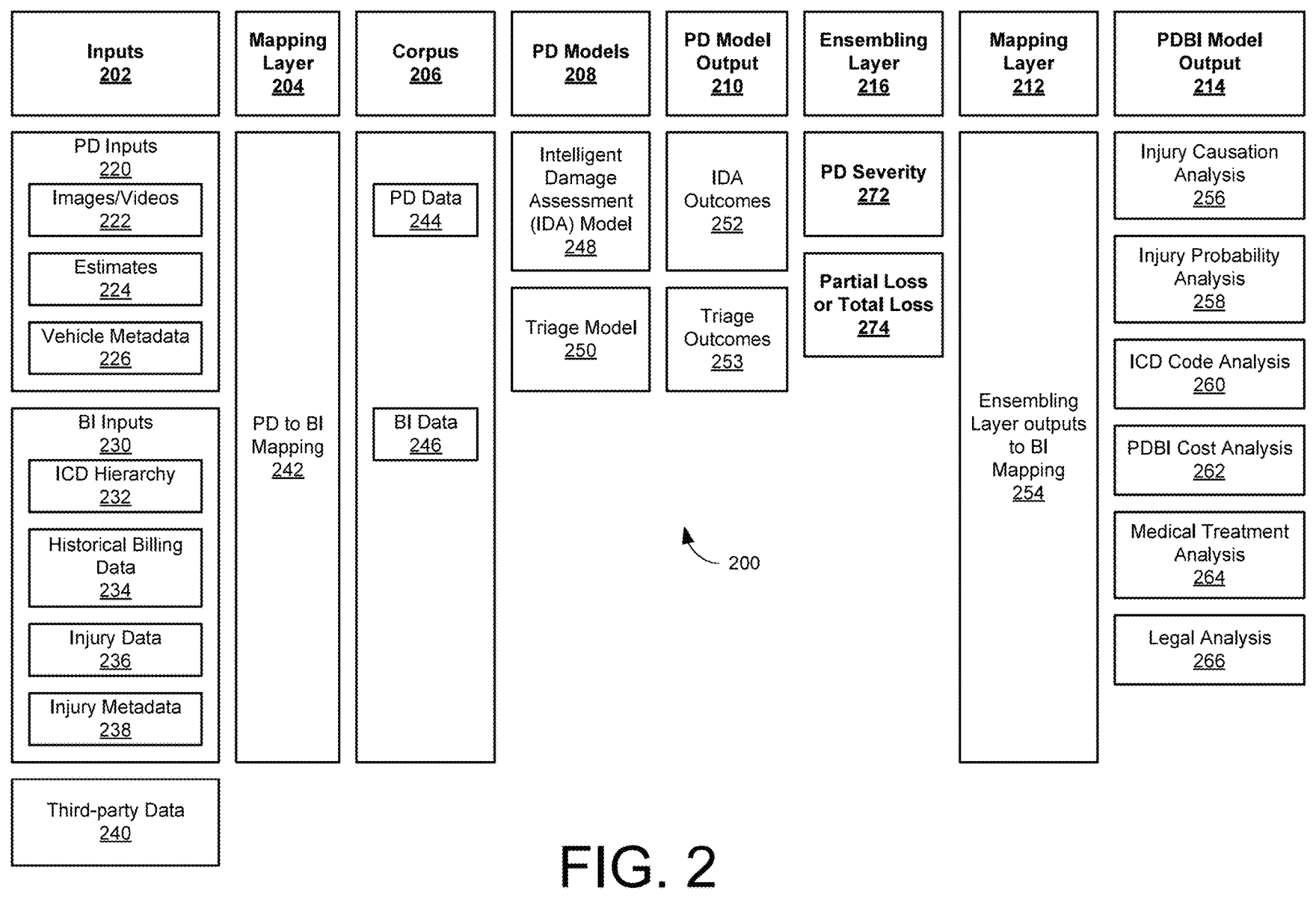

| Inputs 202 | Mapping Layer 204 | Corpus 206 | PD Models 208 | PD Model Output 210 | Ensembling Layer 216 | Mapping Layer 212 | PDBI Model Output 214 |
|---|---|---|---|---|---|---|---|

PD Inputs 220
Images/Videos 222
Estimates 224
Vehicle Metadata 226

BI Inputs 230
ICD Hierarchy 232
Historical Billing Data 234
Injury Data 236
Injury Metadata 238

Third-party Data 240

PD to BI Mapping 242

PD Data 244

BI Data 246

Intelligent Damage Assessment (IDA) Model 248

Triage Model 250

IDA Outcomes 252

Triage Outcomes 253

PD Severity 272

Partial Loss or Total Loss 274

Ensembling Layer outputs to BI Mapping 254

Injury Causation Analysis 256

Injury Probability Analysis 258

ICD Code Analysis 260

PDBI Cost Analysis 262

Medical Treatment Analysis 264

Legal Analysis 266

Injury Causation Analysis

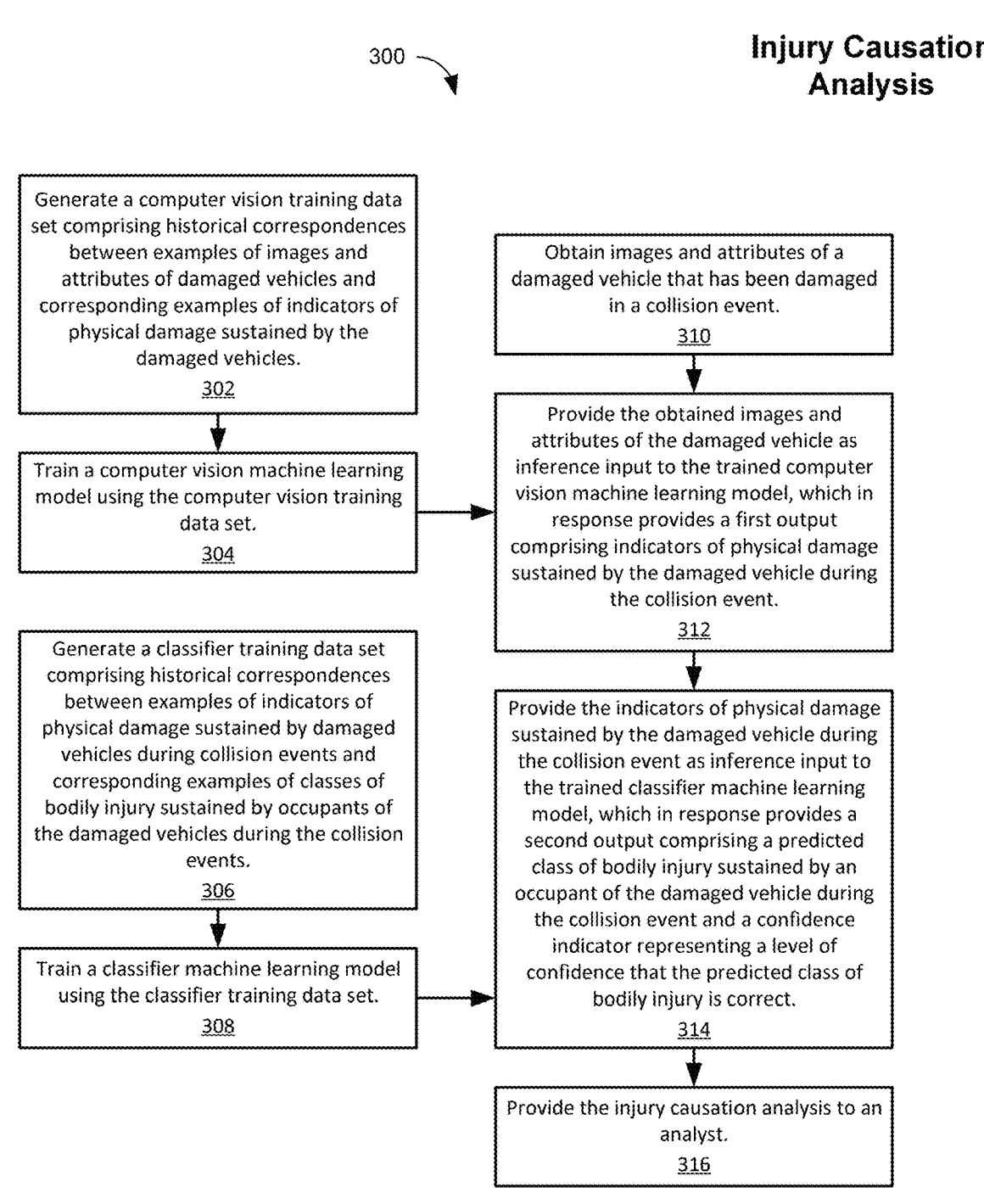

Generate a computer vision training data set comprising historical correspondences between examples of images and attributes of damaged vehicles and corresponding examples of indicators of physical damage sustained by the damaged vehicles.
302

Train a computer vision machine learning model using the computer vision training data set.
304

Generate a classifier training data set comprising historical correspondences between examples of indicators of physical damage sustained by damaged vehicles during collision events and corresponding examples of classes of bodily injury sustained by occupants of the damaged vehicles during the collision events.
306

Train a classifier machine learning model using the classifier training data set.
308

Obtain images and attributes of a damaged vehicle that has been damaged in a collision event.
310

Provide the obtained images and attributes of the damaged vehicle as inference input to the trained computer vision machine learning model, which in response provides a first output comprising indicators of physical damage sustained by the damaged vehicle during the collision event.
312

Provide the indicators of physical damage sustained by the damaged vehicle during the collision event as inference input to the trained classifier machine learning model, which in response provides a second output comprising a predicted class of bodily injury sustained by an occupant of the damaged vehicle during the collision event and a confidence indicator representing a level of confidence that the predicted class of bodily injury is correct.
314

Provide the injury causation analysis to an analyst.
316

Figure 5:
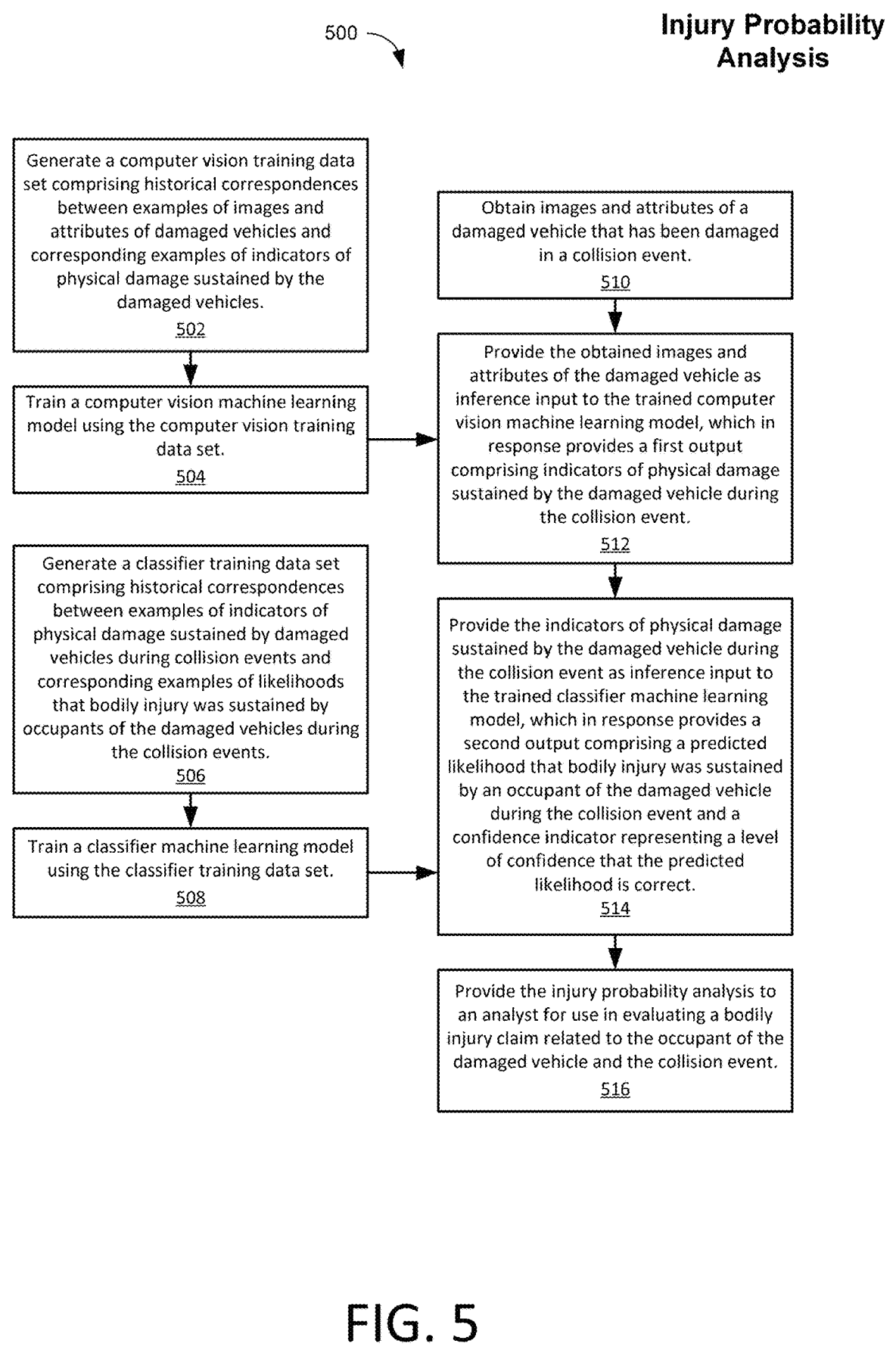

Injury Probability Analysis

Generate a computer vision training data set comprising historical correspondences between examples of images and attributes of damaged vehicles and corresponding examples of indicators of physical damage sustained by the damaged vehicles.
502

↓

Train a computer vision machine learning model using the computer vision training data set.
504

Generate a classifier training data set comprising historical correspondences between examples of indicators of physical damage sustained by damaged vehicles during collision events and corresponding examples of likelihoods that bodily injury was sustained by occupants of the damaged vehicles during the collision events.
506

↓

Train a classifier machine learning model using the classifier training data set.
508

Obtain images and attributes of a damaged vehicle that has been damaged in a collision event.
510

↓

Provide the obtained images and attributes of the damaged vehicle as inference input to the trained computer vision machine learning model, which in response provides a first output comprising indicators of physical damage sustained by the damaged vehicle during the collision event.
512

↓

Provide the indicators of physical damage sustained by the damaged vehicle during the collision event as inference input to the trained classifier machine learning model, which in response provides a second output comprising a predicted likelihood that bodily injury was sustained by an occupant of the damaged vehicle during the collision event and a confidence indicator representing a level of confidence that the predicted likelihood is correct.
514

↓

Provide the injury probability analysis to an analyst for use in evaluating a bodily injury claim related to the occupant of the damaged vehicle and the collision event.
516

ICD Code
Analysis

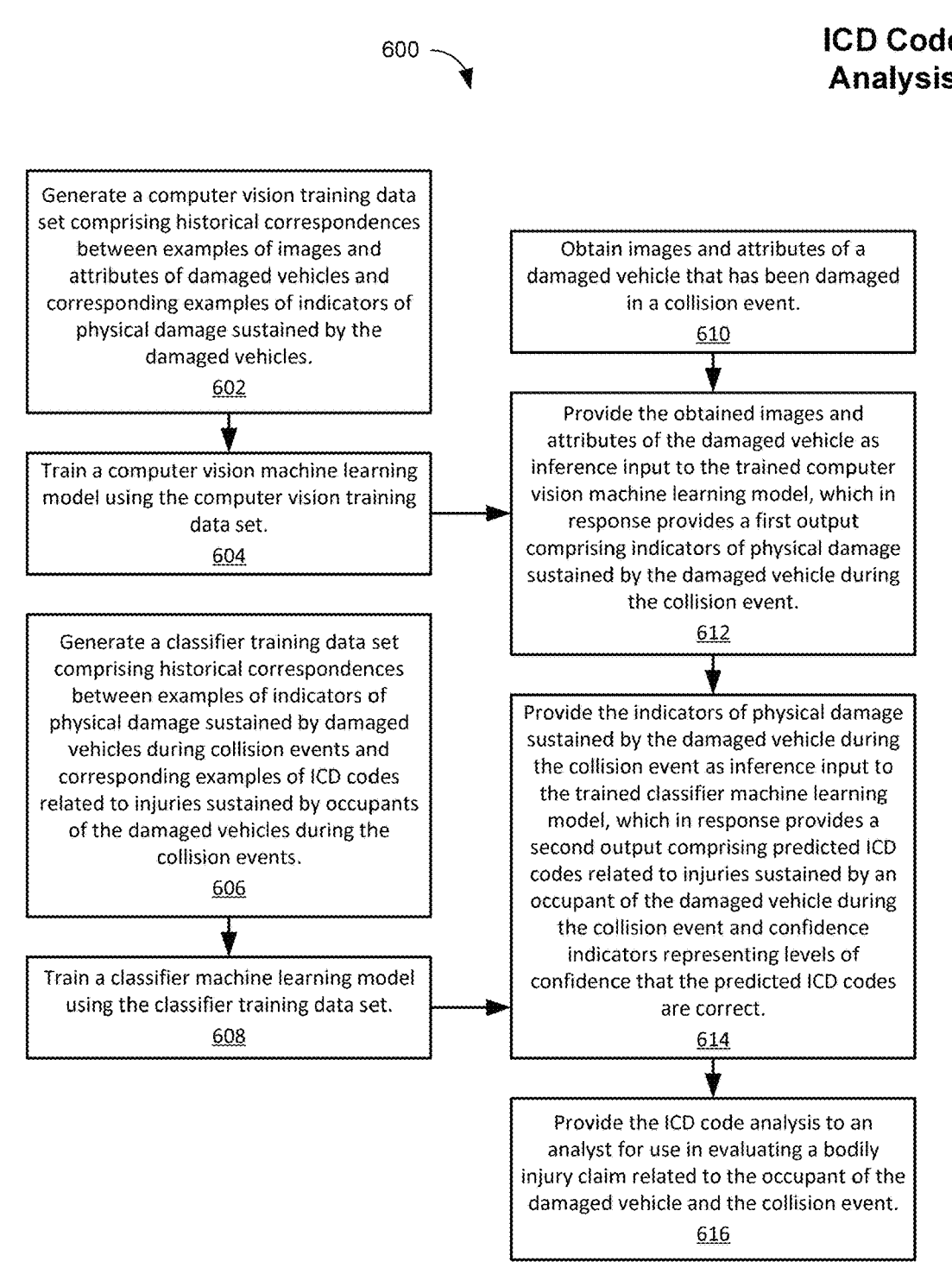

Generate a computer vision training data set comprising historical correspondences between examples of images and attributes of damaged vehicles and corresponding examples of indicators of physical damage sustained by the damaged vehicles.
602

Train a computer vision machine learning model using the computer vision training data set.
604

Generate a classifier training data set comprising historical correspondences between examples of indicators of physical damage sustained by damaged vehicles during collision events and corresponding examples of ICD codes related to injuries sustained by occupants of the damaged vehicles during the collision events.
606

Train a classifier machine learning model using the classifier training data set.
608

Obtain images and attributes of a damaged vehicle that has been damaged in a collision event.
610

Provide the obtained images and attributes of the damaged vehicle as inference input to the trained computer vision machine learning model, which in response provides a first output comprising indicators of physical damage sustained by the damaged vehicle during the collision event.
612

Provide the indicators of physical damage sustained by the damaged vehicle during the collision event as inference input to the trained classifier machine learning model, which in response provides a second output comprising predicted ICD codes related to injuries sustained by an occupant of the damaged vehicle during the collision event and confidence indicators representing levels of confidence that the predicted ICD codes are correct.
614

Provide the ICD code analysis to an analyst for use in evaluating a bodily injury claim related to the occupant of the damaged vehicle and the collision event.
616

Figure 7:
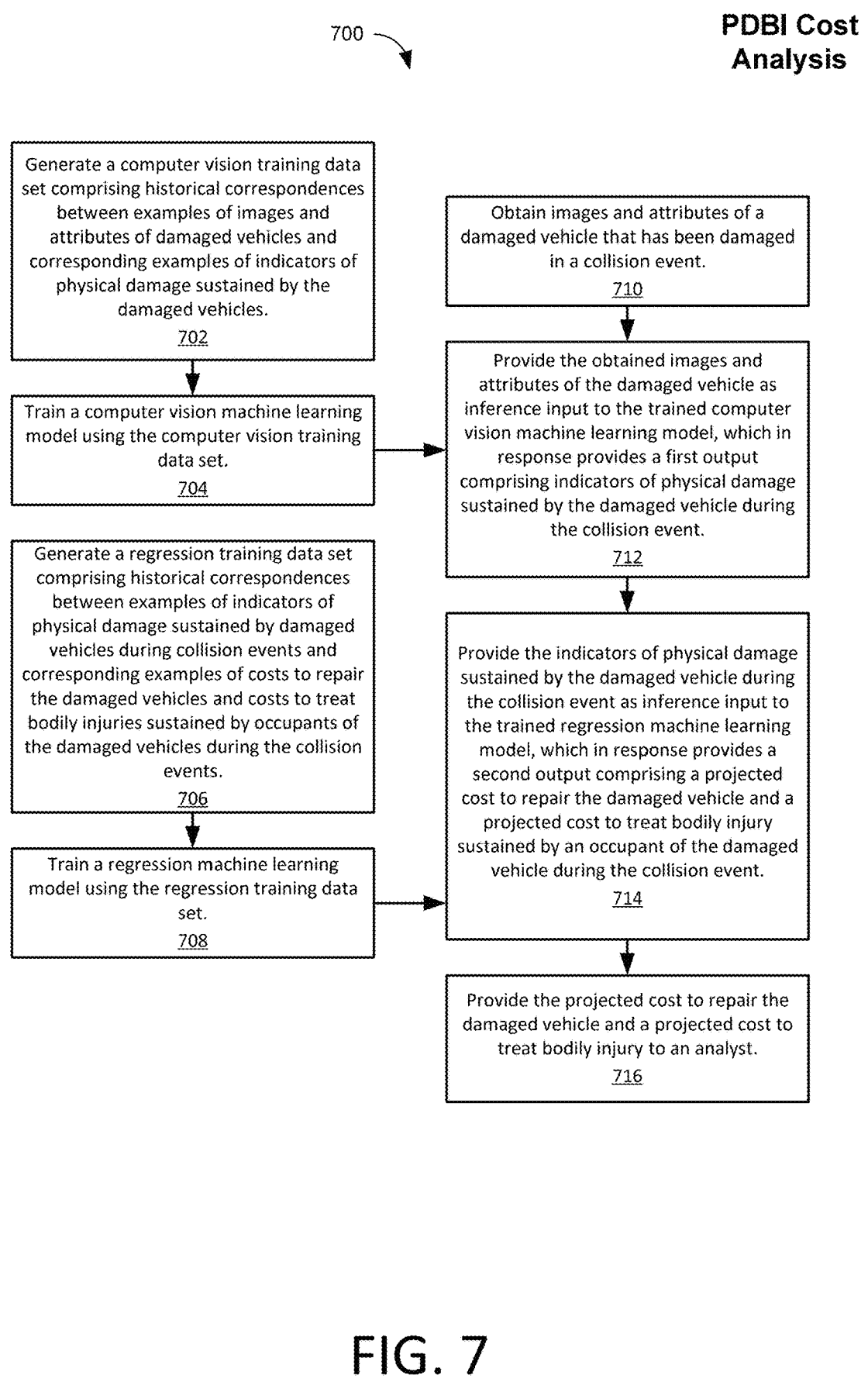

PDBI Cost
Analysis

Generate a computer vision training data set comprising historical correspondences between examples of images and attributes of damaged vehicles and corresponding examples of indicators of physical damage sustained by the damaged vehicles.
702

↓

Train a computer vision machine learning model using the computer vision training data set.
704

Generate a regression training data set comprising historical correspondences between examples of indicators of physical damage sustained by damaged vehicles during collision events and corresponding examples of costs to repair the damaged vehicles and costs to treat bodily injuries sustained by occupants of the damaged vehicles during the collision events.
706

↓

Train a regression machine learning model using the regression training data set.
708

Obtain images and attributes of a damaged vehicle that has been damaged in a collision event.
710

↓

Provide the obtained images and attributes of the damaged vehicle as inference input to the trained computer vision machine learning model, which in response provides a first output comprising indicators of physical damage sustained by the damaged vehicle during the collision event.
712

↓

Provide the indicators of physical damage sustained by the damaged vehicle during the collision event as inference input to the trained regression machine learning model, which in response provides a second output comprising a projected cost to repair the damaged vehicle and a projected cost to treat bodily injury sustained by an occupant of the damaged vehicle during the collision event.
714

↓

Provide the projected cost to repair the damaged vehicle and a projected cost to treat bodily injury to an analyst.
716

Medical Treatment Analysis

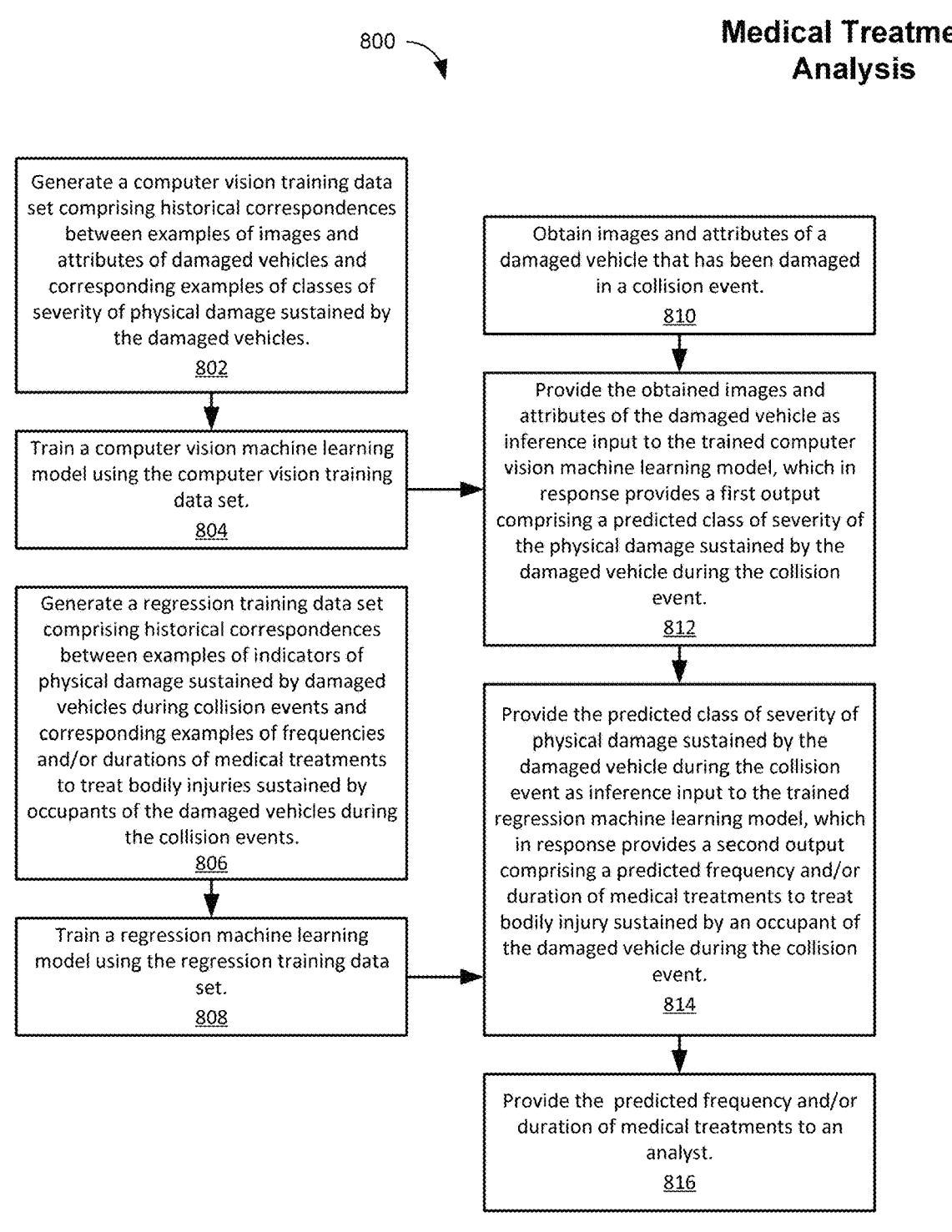

Generate a computer vision training data set comprising historical correspondences between examples of images and attributes of damaged vehicles and corresponding examples of classes of severity of physical damage sustained by the damaged vehicles.
802

Train a computer vision machine learning model using the computer vision training data set.
804

Generate a regression training data set comprising historical correspondences between examples of indicators of physical damage sustained by damaged vehicles during collision events and corresponding examples of frequencies and/or durations of medical treatments to treat bodily injuries sustained by occupants of the damaged vehicles during the collision events.
806

Train a regression machine learning model using the regression training data set.
808

Obtain images and attributes of a damaged vehicle that has been damaged in a collision event.
810

Provide the obtained images and attributes of the damaged vehicle as inference input to the trained computer vision machine learning model, which in response provides a first output comprising a predicted class of severity of the physical damage sustained by the damaged vehicle during the collision event.
812

Provide the predicted class of severity of physical damage sustained by the damaged vehicle during the collision event as inference input to the trained regression machine learning model, which in response provides a second output comprising a predicted frequency and/or duration of medical treatments to treat bodily injury sustained by an occupant of the damaged vehicle during the collision event.
814

Provide the predicted frequency and/or duration of medical treatments to an analyst.
816

FIG. 8

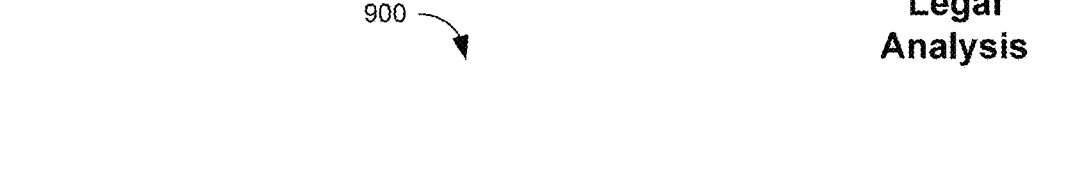

900 ⌐

**Legal
Analysis**

Generate a computer vision training data set comprising historical correspondences between examples of images and attributes of damaged vehicles and corresponding examples of indicators of physical damage sustained by the damaged vehicles.
902

↓

Train a computer vision machine learning model using the computer vision training data set.
904

Generate a classifier training data set comprising historical correspondences between examples of indicators of physical damage sustained by damaged vehicles during collision events and corresponding examples of classes of bodily injury sustained by occupants of the damaged vehicles during the collision events.
906

↓

Train a classifier machine learning model using the classifier training data set.
908

Obtain images and attributes of a damaged vehicle that has been damaged in a collision event.
910

↓

Provide the obtained images and attributes of the damaged vehicle as inference input to the trained computer vision machine learning model, which in response provides a first output comprising indicators of physical damage sustained by the damaged vehicle during the collision event.
912

↓

Provide the indicators of physical damage sustained by the damaged vehicle during the collision event as inference input to the trained classifier machine learning model, which in response provides a second output comprising a predicted class of bodily injury sustained by an occupant of the damaged vehicle during the collision event and a confidence indicator representing a level of confidence that the predicted class of bodily injury is correct.
914

900

**Legal
Analysis**

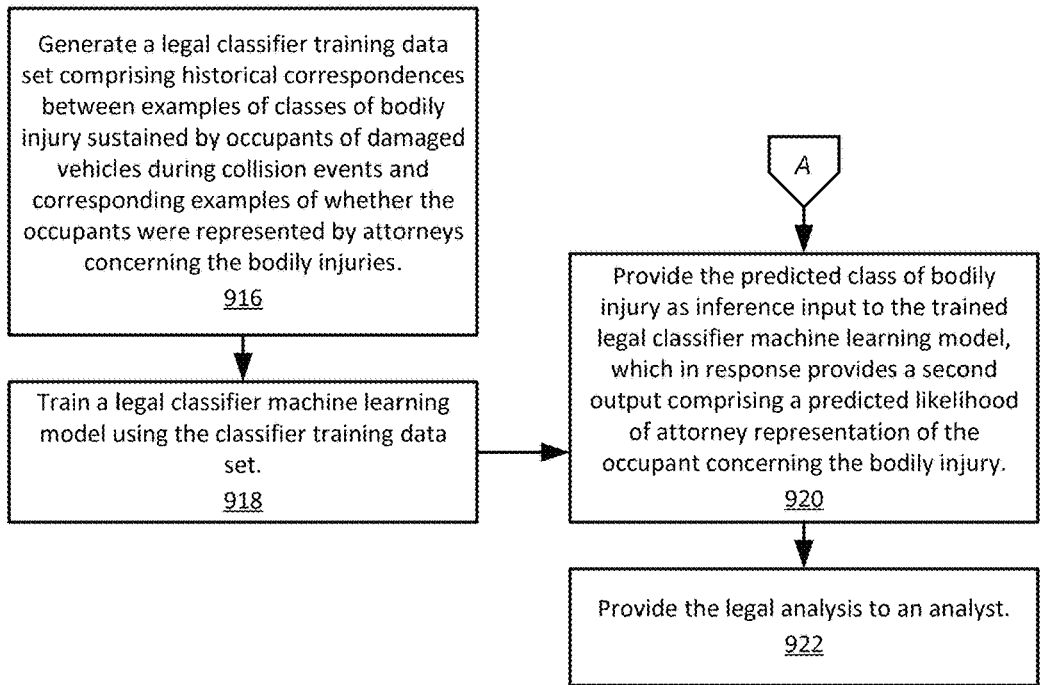

Generate a legal classifier training data set comprising historical correspondences between examples of classes of bodily injury sustained by occupants of damaged vehicles during collision events and corresponding examples of whether the occupants were represented by attorneys concerning the bodily injuries.
916

Train a legal classifier machine learning model using the classifier training data set.
918

A

Provide the predicted class of bodily injury as inference input to the trained legal classifier machine learning model, which in response provides a second output comprising a predicted likelihood of attorney representation of the occupant concerning the bodily injury.
920

Provide the legal analysis to an analyst.
922

| Processor(s) 1004 | | Network Interface(s) 1018 |
|---|---|---|

Bus
1002

| Main Memory 1006 | ROM 1008 | Storage 1010 |
|---|---|---|

| Display 1012 | Input Device(s) 1014 | Cursor Control 1016 |
|---|---|---|

1

PREDICTION OF PROBABILITY OF BODILY INJURY BASED ON VEHICLE DAMAGE

CROSS REFERENCE TO RELATED APPLICATIONS

The present application is related to the following U.S. Patent Applications, the disclosures thereof incorporated by reference herein in their entirety:

U.S. patent application Ser. No. 18/887,362, filed Sep. 17, 2024, entitled "PREDICTION OF BODILY INJURIES AND THEIR SEVERITY BASED ON VEHICLE DAMAGE";

U.S. patent application Ser. No. 18/887,740, filed Sep. 17, 2024, entitled "PREDICTION OF STANDARD MEDICAL DIAGNOSTIC CODES BASED ON VEHICLE DAMAGE";

U.S. patent application Ser. No. 18/887,771, filed Sep. 17, 2024, entitled "COST PROJECTION FOR BOTH PROPERTY DAMAGE AND BODILY INJURY BASED ON VEHICLE DAMAGE";

U.S. patent application Ser. No. 18/887,947, filed Sep. 17, 2024, entitled "PREDICTION OF MEDICAL TREATMENTS FOR BODILY INJURIES BASED ON SEVERITY OF VEHICLE DAMAGE"; and U.S. patent application Ser. No. 18/887,975, filed Sep. 17, 2024, entitled "PREDICTION OF LIKELIHOOD OF ATTORNEY REPRESENTATION BASED ON SEVERITY OF BODILY INJURY".

DESCRIPTION OF RELATED ART

The disclosed technology relates generally to artificial intelligence (AI), and more particularly some embodiments relate to the use of AI in data analyses related to vehicular accidents.

SUMMARY

In general, one aspect disclosed features a system, comprising: one or more hardware processors; and one or more non-transitory machine-readable storage media encoded with instructions that, when executed by the one or more hardware processors, cause the system to perform operations comprising: obtaining images and attributes of a damaged vehicle that has been damaged in a collision event; providing the obtained images and attributes of the damaged vehicle as first inference input to a trained computer vision machine learning model, wherein responsive to the first inference input, the computer vision machine learning model provides a first output comprising indicators of physical damage sustained by the damaged vehicle during the collision event, wherein the trained computer vision machine learning model has been trained with first training data comprising historical correspondences between examples of the first inference input and corresponding examples of the first output; providing the indicators of physical damage sustained by the damaged vehicle during the collision event as second inference input to a trained classifier machine learning model, wherein responsive to the second inference input, the trained classifier machine learning model provides a second output comprising a predicted likelihood that bodily injury was sustained by an occupant of the damaged vehicle during the collision event and a confidence indicator representing a level of confidence that the predicted likelihood that bodily injury was sustained is correct, wherein the predicted likelihood that bodily injury was sustained is one of multiple possible likelihoods of bodily injury, wherein each of the multiple likelihoods of bodily injury indicates a respective likelihood of bodily injury, and wherein the trained classifier machine learning model has been trained with second training data comprising historical correspondences between examples of the second inference input and corresponding examples of the second output; and providing the predicted likelihood of bodily injury and the confidence indicator to an analyst for use in evaluating a bodily injury claim related to the occupant of the damaged vehicle and the collision event.

Embodiments of the system may include one or more of the following features. In some embodiments, the indicators of physical damage sustained by the damaged vehicle during the collision event comprise at least one of: a point of impact that indicates a location where the damaged vehicle collided with a physical object during the collision event; a type of the physical damage sustained by the damaged vehicle during the collision event; a repair cost estimate of a cost of repairing the damage sustained by the damaged vehicle during the collision event; a loss flag indicating whether the damage sustained by the damaged vehicle during the collision event represents a partial loss of the damaged vehicle or a total loss of the damaged vehicle; a fluid flag indicating whether fluid leaked from the damaged vehicle during the collision event; a glass flag indicating whether glass of the damaged vehicle was damaged during the collision event; an airbag flag indicating whether an airbag of the damaged vehicle deployed during the collision event; and a drivable flag indicating whether the damaged vehicle was drivable after the collision event.

In some embodiments, the attributes of the damaged vehicle comprise at least one of: a vehicle identification number (VIN) of the damaged vehicle; make of the damaged vehicle; submodel of the damaged vehicle; model of the damaged vehicle; year or age of the damaged vehicle; mileage of the damaged vehicle; transmission parameters of a transmission of the damaged vehicle; and engine and/or motor parameters of an engine and/or motor of the damaged vehicle.

In some embodiments, the multiple possible predicted likelihoods of bodily injury comprise: a likely predicted likelihood indicating bodily injury is likely; an unlikely predicted likelihood indicating bodily injury is unlikely; and an uncertain predicted likelihood indicating bodily injury is uncertain.

In some embodiments, the operations further comprise: providing occupant metadata as part of the second inference input to the trained classifier machine learning model, wherein the occupant metadata comprises at least one of: an age of the occupant of the damaged vehicle; a height of the occupant of the damaged vehicle; a weight of the occupant of the damaged vehicle; a gender of the occupant of the damaged vehicle; and a role of the occupant of the damaged vehicle in operating the damaged vehicle.

In some embodiments, the operations further comprise: providing collision metadata as part of the second inference input to the trained classifier machine learning model, wherein the collision metadata comprises at least one of: an indicator of the seat in which the occupant was seated in the damaged vehicle during the collision event; an indicator of seatbelt usage for the seat in which the occupant was seated in the damaged vehicle during the collision event; airbag status for the seat in which the occupant was seated in the damaged vehicle during the collision event; and a change in velocity of the damaged vehicle during the collision event.

In some embodiments, the operations further comprise: providing injury claim data representing the bodily injury claim related to the occupant of the damaged vehicle and the collision event as part of the second inference input to the trained classifier machine learning model.

In general, one aspect disclosed features one or more non-transitory machine-readable storage media obtaining images and attributes of a damaged vehicle that has been damaged in a collision event; providing the obtained images and attributes of the damaged vehicle as first inference input to a trained computer vision machine learning model, wherein responsive to the first inference input, the computer vision machine learning model provides a first output comprising indicators of physical damage sustained by the damaged vehicle during the collision event, wherein the trained computer vision machine learning model has been trained with first training data comprising historical correspondences between examples of the first inference input and corresponding examples of the first output; providing the indicators of physical damage sustained by the damaged vehicle during the collision event as second inference input to a trained classifier machine learning model, wherein responsive to the second inference input, the trained classifier machine learning model provides a second output comprising a predicted likelihood that bodily injury was sustained by an occupant of the damaged vehicle during the collision event and a confidence indicator representing a level of confidence that the predicted likelihood that bodily injury was sustained is correct, wherein the predicted likelihood that bodily injury was sustained is one of multiple possible likelihoods of bodily injury, wherein each of the multiple likelihoods of bodily injury indicates a respective likelihood of bodily injury, and wherein the trained classifier machine learning model has been trained with second training data comprising historical correspondences between examples of the second inference input and corresponding examples of the second output; and providing the predicted likelihood of bodily injury and the confidence indicator to an analyst for use in evaluating a bodily injury claim related to the occupant of the damaged vehicle and the collision event.

Embodiments of the one or more non-transitory machine-readable storage media may include one or more of the following features. In some embodiments, the indicators of physical damage sustained by the damaged vehicle during the collision event comprise at least one of: a point of impact that indicates a location where the damaged vehicle collided with a physical object during the collision event; a type of the physical damage sustained by the damaged vehicle during the collision event; a repair cost estimate of a cost of repairing the damage sustained by the damaged vehicle during the collision event; a loss flag indicating whether the damage sustained by the damaged vehicle during the collision event represents a partial loss of the damaged vehicle or a total loss of the damaged vehicle; a fluid flag indicating whether fluid leaked from the damaged vehicle during the collision event; a glass flag indicating whether glass of the damaged vehicle was damaged during the collision event; an airbag flag indicating whether an airbag of the damaged vehicle deployed during the collision event; and a drivable flag indicating whether the damaged vehicle was drivable after the collision event.

In some embodiments, the attributes of the damaged vehicle comprise at least one of: a vehicle identification number (VIN) of the damaged vehicle; make of the damaged vehicle; submodel of the damaged vehicle; model of the damaged vehicle; year or age of the damaged vehicle; mileage of the damaged vehicle; transmission parameters of a transmission of the damaged vehicle; and engine and/or motor parameters of an engine and/or motor of the damaged vehicle.

In some embodiments, the multiple possible predicted likelihoods of bodily injury comprise: a likely predicted likelihood indicating bodily injury is likely; an unlikely predicted likelihood indicating bodily injury is unlikely; and an uncertain predicted likelihood indicating bodily injury is uncertain.

In some embodiments, the operations further comprise: providing occupant metadata as part of the second inference input to the trained classifier machine learning model, wherein the occupant metadata comprises at least one of: an age of the occupant of the damaged vehicle; a height of the occupant of the damaged vehicle; a weight of the occupant of the damaged vehicle; a gender of the occupant of the damaged vehicle; and a role of the occupant of the damaged vehicle in operating the damaged vehicle.

In some embodiments, the operations further comprise: providing collision metadata as part of the second inference input to the trained classifier machine learning model, wherein the collision metadata comprises at least one of: an indicator of the seat in which the occupant was seated in the damaged vehicle during the collision event; an indicator of seatbelt usage for the seat in which the occupant was seated in the damaged vehicle during the collision event; airbag status for the seat in which the occupant was seated in the damaged vehicle during the collision event; and a change in velocity of the damaged vehicle during the collision event.

In some embodiments, the operations further comprise: providing injury claim data representing the bodily injury claim related to the occupant of the damaged vehicle and the collision event as part of the second inference input to the trained classifier machine learning model.

In general, one aspect disclosed features a computer-implemented method, comprising: obtaining images and attributes of a damaged vehicle that has been damaged in a collision event; providing the obtained images and attributes of the damaged vehicle as first inference input to a trained computer vision machine learning model, wherein responsive to the first inference input, the computer vision machine learning model provides a first output comprising indicators of physical damage sustained by the damaged vehicle during the collision event, wherein the trained computer vision machine learning model has been trained with first training data comprising historical correspondences between examples of the first inference input and corresponding examples of the first output; providing the indicators of physical damage sustained by the damaged vehicle during the collision event as second inference input to a trained classifier machine learning model, wherein responsive to the second inference input, the trained classifier machine learning model provides a second output comprising a predicted likelihood that bodily injury was sustained by an occupant of the damaged vehicle during the collision event and a confidence indicator representing a level of confidence that the predicted likelihood that bodily injury was sustained is correct, wherein the predicted likelihood that bodily injury was sustained is one of multiple possible likelihoods of bodily injury, wherein each of the multiple likelihoods of bodily injury indicates a respective likelihood of bodily injury, and wherein the trained classifier machine learning model has been trained with second training data comprising historical correspondences between examples of the second inference input and corresponding examples of the second output; and providing the predicted likelihood of bodily injury and the confidence indicator to an analyst for use in evaluating a bodily injury claim related to the occupant of the damaged vehicle and the collision event.

Embodiments of the computer-implemented method may include one or more of the following features. In some embodiments, the indicators of physical damage sustained by the damaged vehicle during the collision event comprise at least one of: a point of impact that indicates a location where the damaged vehicle collided with a physical object during the collision event; a type of the physical damage sustained by the damaged vehicle during the collision event; a repair cost estimate of a cost of repairing the damage sustained by the damaged vehicle during the collision event; a loss flag indicating whether the damage sustained by the damaged vehicle during the collision event represents a partial loss of the damaged vehicle or a total loss of the damaged vehicle; a fluid flag indicating whether fluid leaked from the damaged vehicle during the collision event; a glass flag indicating whether glass of the damaged vehicle was damaged during the collision event; an airbag flag indicating whether an airbag of the damaged vehicle deployed during the collision event; and a drivable flag indicating whether the damaged vehicle was drivable after the collision event.

In some embodiments, the attributes of the damaged vehicle comprise at least one of: a vehicle identification number (VIN) of the damaged vehicle; make of the damaged vehicle; submodel of the damaged vehicle; model of the damaged vehicle; year or age of the damaged vehicle; mileage of the damaged vehicle; transmission parameters of a transmission of the damaged vehicle; and engine and/or motor parameters of an engine and/or motor of the damaged vehicle.

In some embodiments, the multiple possible predicted likelihoods of bodily injury comprise: a likely predicted likelihood indicating bodily injury is likely; an unlikely predicted likelihood indicating bodily injury is unlikely; and an uncertain predicted likelihood indicating bodily injury is uncertain.

Some embodiments comprise: providing occupant metadata as part of the second inference input to the trained classifier machine learning model, wherein the occupant metadata comprises at least one of: an age of the occupant of the damaged vehicle; a height of the occupant of the damaged vehicle; a weight of the occupant of the damaged vehicle; a gender of the occupant of the damaged vehicle; and a role of the occupant of the damaged vehicle in operating the damaged vehicle.

Some embodiments comprise: providing collision metadata as part of the second inference input to the trained classifier machine learning model, wherein the collision metadata comprises at least one of: an indicator of the seat in which the occupant was seated in the damaged vehicle during the collision event; an indicator of seatbelt usage for the seat in which the occupant was seated in the damaged vehicle during the collision event; airbag status for the seat in which the occupant was seated in the damaged vehicle during the collision event; and a change in velocity of the damaged vehicle during the collision event.

Some embodiments comprise: providing injury claim data representing the bodily injury claim related to the occupant of the damaged vehicle and the collision event as part of the second inference input to the trained classifier machine learning model.

BRIEF DESCRIPTION OF THE DRAWINGS

The present disclosure, in accordance with one or more various embodiments, is described in detail with reference to the following figures. The figures are provided for purposes of illustration only and merely depict typical or example embodiments.

FIG. 2 illustrates a workflow for generating analyses related to vehicular accidents according to some embodiments of the disclosed technology.

FIG. 3 illustrates a process for generating an injury causation analysis according to some embodiments of the disclosed technology.

FIG. 5 illustrates a process for generating an injury probability analysis according to some embodiments of the disclosed technology.

FIG. 6 illustrates a process for generating an ICD code analysis according to some embodiments of the disclosed technology.

FIG. 7 illustrates a process for generating a PDBI Cost Analysis according to some embodiments of the disclosed technology.

FIG. 8 illustrates a process for generating a PDBI Cost Analysis according to some embodiments of the disclosed technology.

FIGS. 9A,B illustrate a process for generating a legal analysis according to some embodiments of the disclosed technology.

Figure 1:
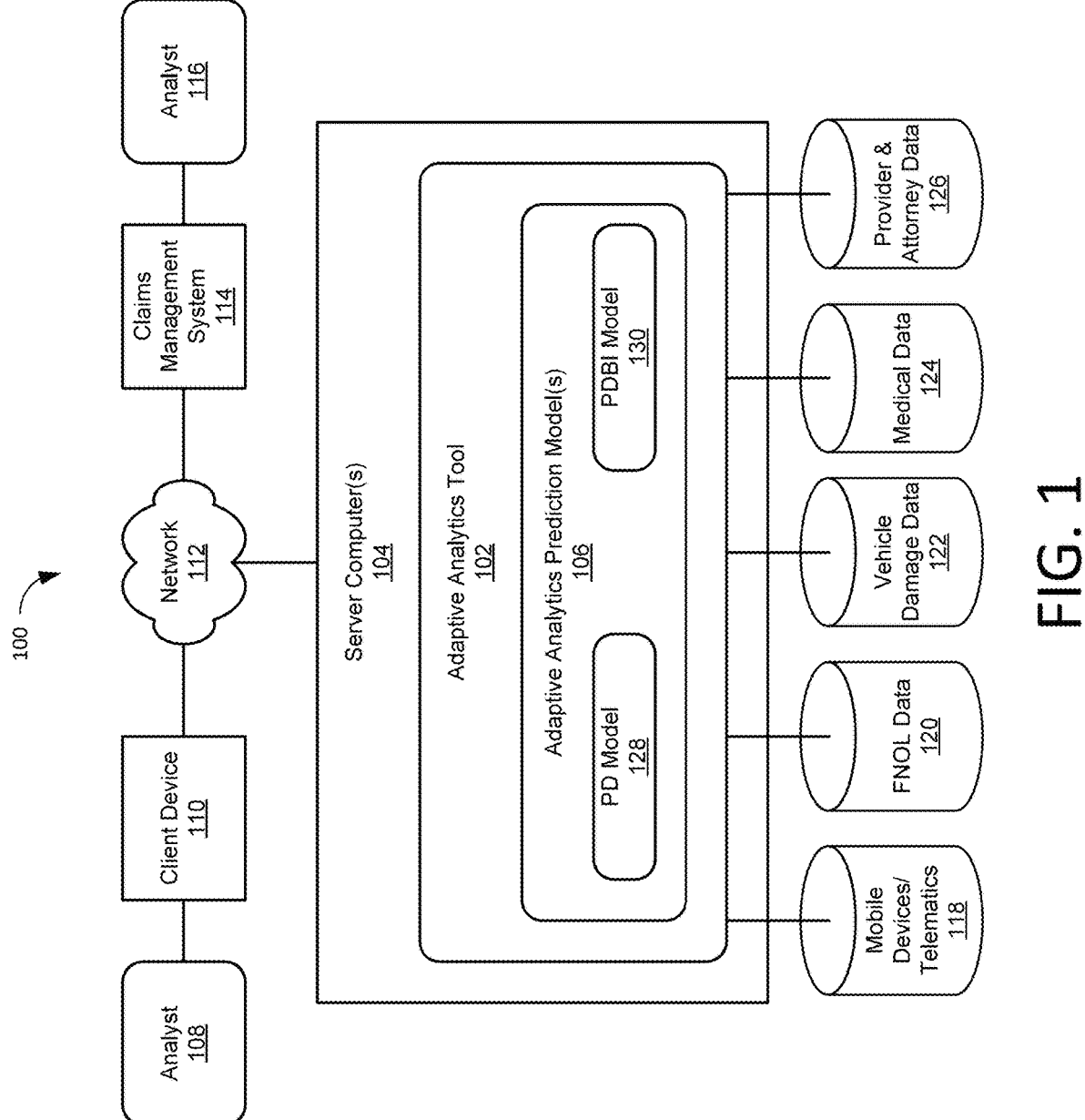
FIG. 1 illustrates an adaptive analytics system for generating analyses related to vehicular accidents according to some embodiments of the disclosed technology.

The figures are not exhaustive and do not limit the present disclosure to the precise form disclosed.

DETAILED DESCRIPTION

Introduction

Claims for bodily injury related to vehicle accidents are on the rise. In particular, low-impact bodily injury claims are rising. In the early 2000s, fraudulent low-impact bodily injury claims were often found to be related to staged accidents. However, recent trends show an uptick in inflated or exaggerated bodily injury claims. Approximately 13-18% of these bodily injury claims are now inflated or exaggerated. For example, an occupant of a vehicle may claim a spinal cord injury when only a small dent is visible on the bumper of the vehicle. As a result, providers may utilize unnecessarily expensive procedures, and may treat conditions that predated the accident. As such, many such claims are litigated. Around 80% of the bodily injury claims that wind up in court are related to these low-impact claims.

In addition, costs related to third-party claims are increasing. For example, these costs rose 14.1% between 2015 and 2017 (cumulative) according to the Insurance Information Institute. As another example, claim severity increased 7.7% while claim frequency dropped 1.1% from 2016 to 2017. According to the National Insurance Crime Bureau (NICB), consumers on average pay an extra $200 to $300 a year in insurance premiums to offset the costs of such fraud. As such, it is becoming more important than ever for analysts to understand the facts regarding these bodily injuries.

Carriers face these and other problems. For example, carrier end-to-end workflows may be inconsistent and inefficient. Carriers also face high turnover in bodily injury analysts. Newer analysts are not medical experts, and again may not have a consistent workflow. Analysts may lack a clear objective, and may lack scientific talking points when negotiating with attorneys. Carriers feel that current analysts may no longer have the necessary skills to analyze bodily injury claims.

These problems have significant effects on carriers. There is greater risk for litigation because of inconsistency in handling claims. The increase in claims costs increases the organization costs and is passed down as a cost to customers in the form of higher premiums.

These problems also have significant effects on claims managers. Due to the increase in complexity of these low-impact injury claims, it takes longer to go through the workflow and therefore it is more difficult to close claims quickly. In addition, the large turnover in the analyst population means that claims managers have to spend more time making sure the analysts are properly trained, and more time hiring new analysts. As a result, claims managers have difficulty setting expectations with customers on claim progress.

Finally, these problems also have significant effects on the analysts. Due to the complexity of these low-impact bodily injury claims, analysts need more time to understand how the injury was caused, or rely upon third parties to provide this information. As a result, analysts are not well-equipped to negotiate against attorneys.

The disclosed embodiments provide tools that help analysts better understand the causation of the bodily injury. These tools improve the carrier's workflow and consistency when dealing with bodily injury claims. Moreover, these tools assist the analyst in analyzing the relationship between physical damage to the vehicle and the claimed bodily injuries. These technical improvements in the technical field of analyzing bodily injury claims also result in lowering the carrier's costs and litigation risk.

FIG. 1 illustrates an adaptive analytics system 100 for generating analyses related to vehicular accidents according to some embodiments of the disclosed technology. Referring to FIG. 1, the system 100 may include an adaptive analytics tool 102 for generating the analyses. The adaptive analytics tool 102 may be implemented as one or more computer programs, and may be hosted on one or more computer servers 104.

The adaptive analytics tool 102 may include one or more adaptive analytics prediction models 106. The models 106 may be implemented as various machine learning models, as described in detail below. For example, the models 106 may include computer vision models, natural language processing models, classifiers, generative models, neural networks, and other machine learning models. The models 106 may include a physical damage (PD) model 128 and a physical damage/bodily injury (PDBI) model 130. The described models may execute on general-purpose or special-purpose computing devices.

An analyst 108 may employ a client device 110 to interact with the adaptive analytics tool 102 over a network 112. The client device 110 may be implemented as a general-purpose or special-purpose computer, a smartphone or tablet, or other computing and interface devices. The network 112 may include any network, including the Internet. In some embodiments, the client device 110 may be connected to the server computer(s) 104 by a direct link.

The adaptive analytics tool 102 may provide the generated analyses to a claims management system 114 for review by an analyst 116. The claims management system 114 may be implemented as one or more computing devices. The adaptive analytics tool 102 may provide the generated analyses to the claims management system 114 over the network 112 or via a direct link.

The adaptive analytics tool 102 may access various data inputs while generating the data analyses. The data inputs may include telematics and similar data, which may be collected by a mobile device, at 118. For example, this data may be collected by apps executing on mobile devices, automotive head units, and the like. This data may include location information, date and time information, data collected by sensors, and the like. For example, the sensor data may include the change in velocity of the vehicle during a collision event.

The data inputs may include first notice of loss (FNOL) data and similar data, which may be collected by a mobile device, at 120. For example, this data may be collected by apps executing on mobile devices, automotive head units, and the like. This data may include facts of loss of a vehicle accident, a triage evaluation of the damage to the vehicle, photos and videos, and additional data concerning the vehicle and any injuries resulting from the accident.

The data inputs may include vehicle damage data, at 122. This data may include photos or videos of vehicle damage and the scene of the accident, cost estimates for repairing physical damage sustained by the vehicle, and data describing point(s) of impact and locations of damage on the vehicle. The data inputs may include vehicle attributes. For example, the vehicle attributes may include actual cash value (ACV) of the vehicle, fair market value (FMV) of the vehicle, mileage of the vehicle, age of the vehicle, and year, make, and model of the vehicle.

The data inputs may include medical data, at 124. This data may include data relating to bodily injury such as injury severity, relatedness of the injury to the accident, and medical treatments for treating injuries sustained during the vehicle accident. Throughout this disclosure, any health and medical data and metadata may strictly adhere to, and be compliant with, privacy regulations such as the Health Insurance Portability and Accountability Act (HIPPA) as protected health information (PHI) of vehicle occupants.

The data inputs may include provider and attorney data, at 126. This data may include data relating to providers of medical treatments, providers of physical damage repair, and providers of legal services. The data may flag involvement of "bad actors", and may visualize linkages.

FIG. 2 illustrates a workflow 200 for generating analyses related to vehicular accidents according to some embodiments of the disclosed technology. The workflow 200 may be executed, for example, by the adaptive analytics system 100 of FIG. 1. In general, the workflow 200 of FIG. 2 proceeds from left to right. However, it should be understood that, in various embodiments, one or more elements may be performed in a different order, in parallel, or omitted. Furthermore, the workflow 200 may include other elements in addition to those presented. For example, the workflow 200 may include error-handling functions if exceptions occur, and the like.

The workflow 200 begins with various inputs 202. These inputs 202 may include inputs 220 related to physical damage (PD), inputs 230 related to bodily injury (BI), and third-party data 240. The PD inputs 220 may include images/and or videos 222 of the damaged vehicle, cost estimates 224 for repair of physical damage to the vehicle, and vehicle metadata 226 concerning the damaged vehicle.

The BI inputs 230 may include a hierarchy 232 of International Classification of Diseases (ICD) codes, historical billing data 234, injury data 236 related to bodily injury, and injury metadata 238 related to the bodily injury. The ICD hierarchy 232 may indicate the nature of the bodily injury, the location of the injury, and the severity of the injury. The historical billing data 234 may indicate the geographical venue of the injury, procedure codes for treatment of the injury, bill charges and amounts paid for treatment of the injury, and dates of service for treatment of the injury. The injury metadata 238 may indicate the venue, the date of injury, and the identity and demographics of the injured vehicle occupant. The injury metadata 238 may be Protected Health Information (PHI) compliant.

The third-party data 240 may include data from the National Automotive Sampling System/Crashworthiness Data System (NASS/CDS), which is provided by the United States National Highway Traffic Safety Administration (NHTSA). The third-party data 240 may include data from the Abbreviated Injury Scale (AIS), which is an anatomical-based coding system created by the Association for the Advancement of Automotive Medicine (AAAM).

The workflow 200 may include a first mapping layer 204. The mapping layer 204 may provide a physical damage to bodily injury mapping 242. The physical damage to bodily injury mapping 242 may include a mapping between physical damage data and bodily injury data.

The workflow 200 may include a corpus 206. The corpus 206 may include physical damage data 244 and bodily injury data 246.

The workflow 200 may include one or more physical damage (PD) models 208. The PD models 208 may include an Intelligent Damage Assessment (IDA) model 248 and a triage model 250. The IDA model 248 may include one or more models that provide physical damage assessments of the damaged vehicle. The triage model 250 may include one or more models that indicate whether the damaged vehicle is a partial loss or a total loss.

The workflow 200 may include outputs 210 of the PD models 208. The PD model outputs 210 may include outcomes 252 provided by the IDA model 248, and outcomes 253 provided by the triage models 250.

The workflow 200 may include an ensembling layer 216 (also referred to as an aggregation layer. The ensembling layer 216 may ingest the outputs 210 of the PD models 208. For example, the ensembling layer 216 may ingest the IDA outcomes 252 and the Triage outcomes 253. From the ingested data, the ensembling layer 216 may derive classes of outcomes such as a classification of PD severity 272 (e.g., low, moderate and, severe) and a classification of partial loss or total loss 274.

The workflow 200 may include a second mapping layer 212. The second mapping layer 212 may include a mapping 254 between the outputs of the ensembling layer 216 and the bodily injury data 246.

The workflow 200 may include outputs 214 of the PDBI model 130 (FIG. 1). These outputs 214 may include an injury causation analysis 256, an injury probability analysis 258, an ICD code analysis 260, a PDBI cost analysis 262, a medical treatment analysis 264, and a legal analysis 266. The generation of each of these analyses is described in detail below.

Injury Causation Analysis

The injury causation analysis 256 may include a prediction of the injuries that would have occurred in the vehicle accident. The injury causation analysis 256 may also include a classification of those injuries by severity. An analyst may employ the predicted injuries and their severities to evaluate injuries claimed by the parties related to the vehicle accident, for example to determine whether these claims are fraudulent.

FIG. 3 illustrates a process 300 for generating an injury causation analysis according to some embodiments of the disclosed technology. The process 300 may be executed, for example, by the adaptive analytics system 100 of FIG. 1. The elements of process 300 are presented in a particular order. However, it should be understood that, in various embodiments, one or more elements may be performed in a different order, in parallel, or omitted. Furthermore, the process 300 may include other elements in addition to those presented. For example, the process 300 may include error-handling functions if exceptions occur, and the like.

Referring to FIG. 3, the process 300 may include generating a computer vision training data set comprising historical correspondences between examples of images and attributes of damaged vehicles and corresponding examples of indicators of physical damage sustained by the damaged vehicles, at 302. Throughout this disclosure, the term "images" is intended to include still images and/or videos.

Referring again to FIG. 3, the process 300 may include training a computer vision machine learning model using the computer vision training data set, at 304. The computer vision machine learning model may be implemented as a convolutional neural network.

Referring again to FIG. 3, the process 300 may include generating a classifier training data set comprising historical correspondences between examples of indicators of physical damage sustained by damaged vehicles during collision events and corresponding examples of classes of bodily injury sustained by occupants of the damaged vehicles during the collision events, at 306.

Referring again to FIG. 3, the process 300 may include training a classifier machine learning model using the classifier training data set, at 308. The training of the classifier machine learning model may include mapping physical damage estimates to bodily injury claims. The training of the classifier machine learning model may include applying labels for injury potential to classes of bodily injury given physical damage patterns.

In some embodiments, the computer vision machine learning model and the classifier machine learning model may be implemented together as a multi-modal model. In such embodiments, the multi-modal model may be trained using both the computer vision training data set and the classifier training data set.

Referring again to FIG. 3, the process 300 may include obtaining images and attributes of a damaged vehicle that has been damaged in a collision event, at 310. Example attributes of the damaged vehicle may include a vehicle identification number (VIN) of the damaged vehicle, make of the damaged vehicle, sub model of the damaged vehicle, model of the damaged vehicle, year or age of the damaged vehicle, mileage of the damaged vehicle, transmission parameters of a transmission of the damaged vehicle, and engine and/or motor parameters of an engine and/or motor of the damaged vehicle. Other attributes of the damaged vehicle may be employed as well.

Referring again to FIG. 3, the process 300 may include providing the obtained images and attributes of the damaged vehicle as inference input to the trained computer vision machine learning model, which in response provides a first output comprising indicators of physical damage sustained by the damaged vehicle during the collision event, at 312. Example indicators of physical damage sustained by the damaged vehicle during the collision event may include a point of impact that indicates a location where the damaged vehicle collided with a physical object during the collision event, a type of the physical damage sustained by the damaged vehicle during the collision event, a repair cost estimate of a cost of repairing the damage sustained by the damaged vehicle during the collision event, a loss flag indicating whether the damage sustained by the damaged vehicle during the collision event represents a partial loss of the damaged vehicle or a total loss of the damaged vehicle, a fluid flag indicating whether fluid leaked from the damaged vehicle during the collision event, a glass flag indicating whether glass of the damaged vehicle was damaged during the collision event, an airbag flag indicating whether an airbag of the damaged vehicle deployed during the collision event, and a drivable flag indicating whether the damaged vehicle was drivable after the collision event. Other indicators of physical damage sustained by the damaged vehicle during the collision event may be employed as well.

Referring again to FIG. 3, the process 300 may include providing the indicators of physical damage sustained by the damaged vehicle during the collision event as inference input to the trained classifier machine learning model, which in response provides a second output comprising a predicted class of bodily injury sustained by an occupant of the damaged vehicle during the collision event and a confidence indicator representing a level of confidence that the predicted class of bodily injury is correct, at 314. The predicted class of bodily injury may be one of multiple possible predicted classes of bodily injury. Each of the multiple possible predicted classes of bodily injury may indicate a respective severity of bodily injury. Example classes of bodily injury may include a no injury class indicating no bodily injury, a moderate injury class indicating moderate bodily injury, and a severe injury class indicating severe bodily injury. Other classes of bodily injury may be employed as well.

In some embodiments, the indicators of physical damage sustained by the damaged vehicle during the collision event include a physical damage severity class indicating a severity of the physical damage. In such embodiments, the output of the trained classifier machine learning model may include a correlation indicator indicating a degree of correlation between the predicted class of bodily injury and the physical damage severity class.

In some embodiments, occupant metadata may be provided as part of the inference input to the trained classifier machine learning model. The occupant metadata may be Protected Health Information (PHI) compliant. Example occupant metadata may include an age of the occupant of the damaged vehicle, a height of the occupant of the damaged vehicle, a weight of the occupant of the damaged vehicle, a gender of the occupant of the damaged vehicle, and a role of the occupant of the damaged vehicle in operating the damaged vehicle. Other occupant metadata may be employed as well.

In some embodiments, collision metadata may be provided as part of the inference input to the trained classifier machine learning model. Example collision metadata may include an indicator of the seat in which the occupant was seated in the damaged vehicle during the collision event, an indicator of seatbelt usage for the seat in which the occupant was seated in the damaged vehicle during the collision event, airbag status for the seat in which the occupant was seated in the damaged vehicle during the collision event, and a change in velocity of the damaged vehicle during the collision event. Other collision metadata may be employed as well.

In some embodiments, injury claim data representing the bodily injury claim related to the occupant of the damaged vehicle and the collision event may be provided as part of the inference input to the trained classifier machine learning model.

Figure 4:
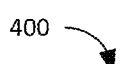
FIG. 4. depicts an example user interface showing heat maps of physical damage and bodily injury according to some embodiments of the disclosed technology.

In some embodiments, output of the trained classifier machine learning model may include a mapping of locations of vehicle physical damage to locations of bodily injury. The mapping may include a heat map. FIG. 4. depicts an example user interface 400 showing heat maps of physical damage and bodily injury according to some embodiments of the disclosed technology. The upper panel of the example user interface 400 depicts point-of-impact data in a heat map format, at 402. The upper panel also presents flags indicating whether the vehicle was drivable after the accident, at 404, whether airbags were deployed during the accident, at 406, and whether seatbelts were worn during the accident, at 408. The lower panel depicts bodily injury location in heat map format, at 410, and as a textual description, including the severity of each injury, at 412. The lower panel includes a user-operable display element, at 414, that enables an analyst to enter additional injuries.

Referring again to FIG. 3, the process 300 may include providing the injury causation analysis 256 to an analyst, at 316. The analyst may employ the injury causation analysis 256 in evaluating a bodily injury claim related to the occupant of the damaged vehicle and the collision event. In some embodiments, the injury causation analysis 256 may include the predicted class of bodily injury and the related confidence indicator.

In some embodiments, the injury causation analysis 256 may include a probabilistic score of injury severity. In some embodiments, the injury causation analysis 256 may include a probabilistic score relating injury likelihood to partial loss or total loss of the vehicle. In some embodiments, the injury causation analysis 256 may include a mapping of locations of vehicle physical damage to locations of bodily injury, for example as described above with reference to FIG. 4. In some embodiments, the injury causation analysis 256 may include the damage photos.

The injury causation analysis 256 provides several advantages. By providing a predicted class of bodily injury, the injury causation analysis 256 improves the adjuster's ability to analyze bodily injury claims. Use of the injury causation analysis 256 may improve cycle time efficiency, while providing explainable, transparent, and bias free consistent decisions which are highly accurate. And by providing confidence indicators representing levels of confidence that the predicted class of bodily injury is correct, the injury causation analysis 256 helps the adjuster improve the accuracy of bodily injury claims.

Injury Probability Analysis

The injury probability analysis 258 may include a probability of occurrence of the injuries that would have occurred in the vehicle accident. The injury probability analysis 258 may also include a classification of those injuries by severity. An analyst may employ the injury probability to evaluate injuries claimed by parties related to the vehicle accident, for example to determine whether these claims are fraudulent.

FIG. 5 illustrates a process 500 for generating an injury probability analysis according to some embodiments of the disclosed technology. The process 500 may be executed, for example, by the adaptive analytics system 100 of FIG. 1. The elements of process 500 are presented in a particular order. However, it should be understood that, in various embodiments, one or more elements may be performed in a different order, in parallel, or omitted. Furthermore, the process 500 may include other elements in addition to those presented. For example, the process 500 may include error-handling functions if exceptions occur, and the like.

Referring to FIG. 5, the process 500 may include generating a computer vision training data set comprising historical correspondences between examples of images and/or videos and attributes of damaged vehicles and corresponding examples of indicators of physical damage sustained by the damaged vehicles, at 502.

Referring again to FIG. 5, the process 500 may include training a computer vision machine learning model using the computer vision training data set, at 504. The computer vision machine learning model may be implemented as a convolutional neural network.

Referring again to FIG. 5, the process 500 may include generating a classifier training data set comprising historical correspondences between examples of indicators of physical damage sustained by damaged vehicles during collision events and corresponding examples of likelihoods that bodily injury was sustained by occupants of the damaged vehicles during the collision events, at 506.

Referring again to FIG. 5, the process 500 may include training a classifier machine learning model using the classifier training data set, at 508. The training of the classifier machine learning model may include mapping physical damage estimates to bodily injury claims. The training of the classifier machine learning model may include applying labels for injury potential to likelihoods of bodily injury given physical damage patterns.

In some embodiments, the computer vision machine learning model and the classifier machine learning model may be implemented together as a multi-modal model. In such embodiments, the multi-modal model may be trained using both the computer vision training data set and the classifier training data set.

Referring again to FIG. 5, the process 500 may include obtaining images and attributes of a damaged vehicle that has been damaged in a collision event, at 510. Example attributes of the damaged vehicle may include a vehicle identification number (VIN) of the damaged vehicle, make of the damaged vehicle, sub model of the damaged vehicle, model of the damaged vehicle, year or age of the damaged vehicle, mileage of the damaged vehicle, transmission parameters of a transmission of the damaged vehicle, and engine and/or motor parameters of an engine and/or motor of the damaged vehicle. Other attributes of the damaged vehicle may be employed as well.

Referring again to FIG. 5, the process 500 may include providing the obtained images and attributes of the damaged vehicle as inference input to the trained computer vision machine learning model, which in response provides a first output comprising indicators of physical damage sustained by the damaged vehicle during the collision event, at 512. Example indicators of physical damage sustained by the damaged vehicle during the collision event may include a point of impact that indicates a location where the damaged vehicle collided with a physical object during the collision event, a type of the physical damage sustained by the damaged vehicle during the collision event, a repair cost estimate of a cost of repairing the damage sustained by the damaged vehicle during the collision event, a loss flag indicating whether the damage sustained by the damaged vehicle during the collision event represents a partial loss of the damaged vehicle or a total loss of the damaged vehicle, a fluid flag indicating whether fluid leaked from the damaged vehicle during the collision event, a glass flag indicating whether glass of the damaged vehicle was damaged during the collision event, an airbag flag indicating whether an airbag of the damaged vehicle deployed during the collision event, and a drivable flag indicating whether the damaged vehicle was drivable after the collision event. Other indicators of physical damage sustained by the damaged vehicle during the collision event may be employed as well.

Referring again to FIG. 5, the process 500 may include providing the indicators of physical damage sustained by the damaged vehicle during the collision event as inference input to the trained classifier machine learning model, which in response provides a second output comprising a predicted likelihood that bodily injury was sustained by an occupant of the damaged vehicle during the collision event and a confidence indicator representing a level of confidence that the predicted likelihood of bodily injury is correct, at 514. The predicted likelihood of bodily injury may be one of multiple possible predicted likelihoods of bodily injury. Each of the multiple possible predicted likelihoods of bodily injury may indicate a respective severity of bodily injury. Example predicted likelihoods may include a likely predicted likelihood indicating bodily injury is likely, an unlikely predicted likelihood indicating bodily injury is unlikely, and an uncertain predicted likelihood indicating bodily injury is uncertain. Other predicted likelihoods may be employed as well.

In some embodiments, the indicators of physical damage sustained by the damaged vehicle during the collision event include a physical damage severity class indicating a severity of the physical damage. In such embodiments, the output of the trained classifier machine learning model may include a correlation indicator indicating a degree of correlation between the predicted class of bodily injury and the physical damage severity class.

In some embodiments, PHI compliant occupant metadata may be provided as part of the inference input to the trained classifier machine learning model. Example occupant metadata may include an age of the occupant of the damaged vehicle, a height of the occupant of the damaged vehicle, a weight of the occupant of the damaged vehicle, a gender of the occupant of the damaged vehicle, and a role of the occupant of the damaged vehicle in operating the damaged vehicle. Other occupant metadata may be employed as well.

In some embodiments, collision metadata may be provided as part of the inference input to the trained classifier machine learning model. Example collision metadata may include an indicator of the seat in which the occupant was seated in the damaged vehicle during the collision event (PHI compliant), an indicator of seatbelt usage for the seat in which the occupant was seated in the damaged vehicle during the collision event, airbag status for the seat in which the occupant was seated in the damaged vehicle during the collision event, and a change in velocity of the damaged vehicle during the collision event. Other collision metadata may be employed as well.

In some embodiments, injury claim data representing the bodily injury claim related to the occupant of the damaged vehicle and the collision event may be provided as part of the inference input to the trained classifier machine learning model.

Referring again to FIG. 5, the process 500 may include providing the injury probability analysis 258 in FIG. 2 to an analyst, at 516, in FIG. 5. The analyst may employ the injury probability analysis 258 in evaluating a bodily injury claim related to the occupant of the damaged vehicle and the collision event. In some embodiments, the injury probability analysis 258 may include the likelihood of bodily injury and a confidence indicator.

In some embodiments, the injury probability analysis 258, in FIG. 2 may include a probabilistic score/binary classification of injury likelihood. In some embodiments, the injury probability analysis 258 may include a probabilistic score relating injury likelihood to partial loss or total loss of the vehicle. In some embodiments, the injury probability analysis 258 may include a mapping of locations of vehicle physical damage to locations of bodily injury, for example as described above with reference to FIG. 4. In some embodiments, the injury probability analysis 258 may include the damage photos and/or video frames of relevance.

The injury probability analysis 258 provides several advantages. By providing a likelihood of bodily injury, the injury probability analysis 258 improves the adjuster's ability to analyze bodily injury claims. And by providing confidence indicators representing levels of confidence that the likelihood of bodily injury is correct, the injury probability analysis 258 helps the adjuster improve the accuracy of bodily injury claims. Use of the injury probability analysis 258 may improve cycle time efficiency, while providing explainable, transparent, and bias free consistent decisions which are highly accurate.

ICD Code Analysis

The ICD code analysis 260 may include recommended likely International Classification of Diseases (ICD) codes for injuries sustained during a vehicle accident. It should be understood that, while the described embodiments employ ICD codes, other embodiments may employ other sets of standard medical diagnostic codes instead of, or in addition to, ICD codes. An analyst may employ the recommended likely ICD codes to evaluate injury claims submitted by the parties related to the vehicle accident, for example to determine whether these claims are fraudulent or whether ICD codes are missing from the claim.

FIG. 6 illustrates a process 600 for generating an ICD code analysis according to some embodiments of the disclosed technology. The process 600 may be executed, for example, by the adaptive analytics system 100 of FIG. 1. The elements of process 600 are presented in a particular order. However, it should be understood that, in various embodiments, one or more elements may be performed in a different order, in parallel, or omitted. Furthermore, the process 600 may include other elements in addition to those presented. For example, the process 600 may include error-handling functions if exceptions occur, and the like.

Referring to FIG. 6, the process 600 may include generating a computer vision training data set comprising historical correspondences between examples of images and attributes of damaged vehicles and corresponding examples of indicators of physical damage sustained by the damaged vehicles, at 602.

Referring again to FIG. 6, the process 600 may include training a computer vision machine learning model using the computer vision training data set, at 604. The computer vision machine learning model may be implemented as a convolutional neural network.

Referring again to FIG. 6, the process 600 may include generating a classifier training data set comprising historical correspondences between examples of indicators of physical damage sustained by damaged vehicles during collision events and corresponding examples of ICD codes related to injuries sustained by occupants of the damaged vehicles during the collision events, at 606.

Referring again to FIG. 6, the process 600 may include training a classifier machine learning model using the classifier training data set, at 608. The training of the classifier machine learning model may include mapping physical damage estimates to bodily injury claims.

In some embodiments, the computer vision machine learning model and the classifier machine learning model may be implemented together as a multi-modal model. In such embodiments, the multi-modal model may be trained using both the computer vision training data set and the classifier training data set.

Referring again to FIG. 6, the process 600 may include obtaining images and attributes of a damaged vehicle that has been damaged in a collision event, at 610. Example attributes of the damaged vehicle may include a vehicle identification number (VIN) of the damaged vehicle, make of the damaged vehicle, sub model of the damaged vehicle, model of the damaged vehicle, year or age of the damaged vehicle, mileage of the damaged vehicle, transmission parameters of a transmission of the damaged vehicle, and engine and/or motor parameters of an engine and/or motor of the damaged vehicle. Other attributes of the damaged vehicle may be employed as well.

Referring again to FIG. 6, the process 600 may include providing the obtained images and attributes of the damaged vehicle as inference input to the trained computer vision machine learning model, which in response provides a first output comprising indicators of physical damage sustained by the damaged vehicle during the collision event, at 612. Example indicators of physical damage sustained by the damaged vehicle during the collision event may include a point of impact that indicates a location where the damaged vehicle collided with a physical object during the collision event, a type of the physical damage sustained by the damaged vehicle during the collision event, a repair cost estimate of a cost of repairing the damage sustained by the damaged vehicle during the collision event, a loss flag indicating whether the damage sustained by the damaged vehicle during the collision event represents a partial loss of the damaged vehicle or a total loss of the damaged vehicle, a fluid flag indicating whether fluid leaked from the damaged vehicle during the collision event, a glass flag indicating whether glass of the damaged vehicle was damaged during the collision event, an airbag flag indicating whether an airbag of the damaged vehicle deployed during the collision event, and a drivable flag indicating whether the damaged vehicle was drivable after the collision event. Other indicators of physical damage sustained by the damaged vehicle during the collision event may be employed as well.

Referring again to FIG. 6, the process 600 may include providing the indicators of physical damage sustained by the damaged vehicle during the collision event as inference input to the trained classifier machine learning model, which in response provides a second output comprising predicted ICD codes related to injuries sustained by an occupant of the damaged vehicle during the collision event and confidence indicators representing levels of confidence that the predicted ICD codes are correct, at 614. The predicted likelihood of bodily injury may be one of multiple possible predicted likelihoods of bodily injury. Each of the multiple possible predicted likelihoods of bodily injury may indicate a respective severity of bodily injury. Example predicted likelihoods may include a likely predicted likelihood indicating bodily injury is likely, an unlikely predicted likelihood indicating bodily injury is unlikely, and an uncertain predicted likelihood indicating bodily injury is uncertain. Other predicted likelihoods may be employed as well.

In some embodiments, the indicators of physical damage sustained by the damaged vehicle during the collision event include a physical damage severity class indicating a severity of the physical damage. In such embodiments, the output of the trained classifier machine learning model may include a correlation indicator indicating a degree of correlation between the predicted class of bodily injury and the physical damage severity class.

In some embodiments, PHI-compliant occupant metadata may be provided as part of the inference input to the trained classifier machine learning model. Example occupant metadata may include an age of the occupant of the damaged vehicle, a height of the occupant of the damaged vehicle, a weight of the occupant of the damaged vehicle, a gender of the occupant of the damaged vehicle, and a role of the occupant of the damaged vehicle in operating the damaged vehicle. Other occupant metadata may be employed as well.

In some embodiments, collision metadata may be provided as part of the inference input to the trained classifier machine learning model. Example collision metadata may include an indicator of the seat in which the occupant was seated in the damaged vehicle during the collision event, an indicator of seatbelt usage for the seat in which the occupant was seated in the damaged vehicle during the collision event, airbag status for the seat in which the occupant was seated in the damaged vehicle during the collision event, and a change in velocity of the damaged vehicle during the collision event. Other collision metadata may be employed as well.

In some embodiments, injury claim data representing the bodily injury claim related to the occupant of the damaged vehicle and the collision event may be provided as part of the inference input to the trained classifier machine learning model.

In some embodiments, output of the trained classifier machine learning model may include a mapping of locations of vehicle physical damage to locations of bodily injury, for example as described above with reference to FIG. 4.

Referring again to FIG. 6, the process 600 may include providing the ICD code analysis 260 of FIG. 2 to an analyst, at 616 of FIG. 6. The analyst may employ the ICD code analysis 260 in evaluating a bodily injury claim related to the occupant of the damaged vehicle and the collision event. In some embodiments, the ICD code analysis 260 may flag as not relevant those predicted ICD codes having confidence indicators that do not exceed a predetermined threshold. In some embodiments, the ICD code analysis 260 may provide an itemized list of likely codes relevant to occupants of the damaged vehicles and the collision event with an itemized confidence indicator. In such embodiments, high confidence ICD codes may be ranked and ordered, while low confidence ICD codes may be removed if they did not exceed predetermined confidence thresholds. The predetermined thresholds may also be configurable for a given classification of vehicle damage. In some embodiments, the ICD code analysis 260 may be used as a recommendations engine for ICD class of codes for a given class of vehicle damage, including characteristics of vehicle damage such as point of impact, vehicle age, occupant age, and the like. In some embodiments, the ICD code analysis 260 may include only those predicted ICD codes having confidence scores above a certain threshold. In some embodiments, the ICD code analysis 260 may include the damage photos. In some embodiments, the ICD code analysis 260 may include a probabilistic score relating injury likelihood to partial loss or total loss of the vehicle.

The ICD code analysis 260 provides several advantages. By providing predicted ICD codes related to bodily injury injuries, the ICD code analysis 260 improves the adjuster's ability to analyze bodily injury claims. And by providing confidence indicators representing levels of confidence that the predicted ICD codes are correct, the ICD code analysis 260 helps the adjuster improve the accuracy of bodily injury claims. Use of the ICD code analysis 260 may improve cycle time efficiency, while providing explainable, transparent, and bias free consistent decisions which are highly accurate.

PDBI Cost Analysis

The physical damage/bodily injury (PDBI) cost analysis 262 may include a projected cost to treat bodily injury to an analyst for use in evaluating a bodily injury claim related to an occupant of a damaged vehicle during a collision event and a damaged vehicle physical damage claim related to the collision event. An analyst may employ the PDBI cost analysis 262 to evaluate bodily injury claims submitted by the occupant and physical damage claims for the damaged vehicle, for example to determine whether these claims are in line with the costs or are fraudulent.

FIG. 7 illustrates a process 700 for generating a PDBI Cost Analysis according to some embodiments of the disclosed technology. The process 700 may be executed, for example, by the adaptive analytics system 100 of FIG. 1. The elements of process 700 are presented in a particular order. However, it should be understood that, in various embodiments, one or more elements may be performed in a different order, in parallel, or omitted. Furthermore, the process 700 may include other elements in addition to those presented. For example, the process 700 may include error-handling functions if exceptions occur, and the like.

Referring to FIG. 7, the process 700 may include generating a computer vision training data set comprising historical correspondences between examples of images and attributes of damaged vehicles and corresponding examples of indicators of physical damage sustained by the damaged vehicles, at 702.

Referring again to FIG. 7, the process 700 may include training a computer vision machine learning model using the computer vision training data set, at 704. The computer vision machine learning model may be implemented as a convolutional neural network.

Referring again to FIG. 7, the process 700 may include generating a regression training data set comprising historical correspondences between examples of indicators of physical damage sustained by damaged vehicles during collision events and corresponding examples of costs to repair the damaged vehicles and costs to treat bodily injuries sustained by occupants of the damaged vehicles during the collision events, at 706.

Referring again to FIG. 7, the process 700 may include training a regression machine learning model using the regression training data set, at 708. The training may take the form of supervised learning, where input features and output labels are associated in the regression training data set. The regression machine learning model may be in addition to the image damage analysis classification model.

In some embodiments, the computer vision machine learning model and the regression machine learning model may be implemented together as a multi-modal model. In such embodiments, the multi-modal model may be trained using both the computer vision training data set and the regression training data set.

Referring again to FIG. 7, the process 700 may include obtaining images and attributes of a damaged vehicle that has been damaged in a collision event, at 710. Example attributes of the damaged vehicle may include a vehicle identification number (VIN) of the damaged vehicle, make of the damaged vehicle, sub model of the damaged vehicle, model of the damaged vehicle, year or age of the damaged vehicle, mileage of the damaged vehicle, transmission parameters of a transmission of the damaged vehicle, and engine and/or motor parameters of an engine and/or motor of the damaged vehicle. Other attributes of the damaged vehicle may be employed as well.

Referring again to FIG. 7, the process 700 may include providing the obtained images and attributes of the damaged vehicle as inference input to the trained computer vision machine learning model, which in response provides a first output comprising indicators of physical damage sustained by the damaged vehicle during the collision event, at 712. Example indicators of physical damage sustained by the damaged vehicle during the collision event may include a point of impact that indicates a location where the damaged vehicle collided with a physical object during the collision event, a type of the physical damage sustained by the damaged vehicle during the collision event, a repair cost estimate of a cost of repairing the damage sustained by the damaged vehicle during the collision event, a loss flag indicating whether the damage sustained by the damaged vehicle during the collision event represents a partial loss of the damaged vehicle or a total loss of the damaged vehicle, a fluid flag indicating whether fluid leaked from the damaged vehicle during the collision event, a glass flag indicating whether glass of the damaged vehicle was damaged during the collision event, an airbag flag indicating whether an airbag of the damaged vehicle deployed during the collision event, and a drivable flag indicating whether the damaged vehicle was drivable after the collision event. Other indicators of physical damage sustained by the damaged vehicle during the collision event may be employed as well.

Referring again to FIG. 7, the process 700 may include providing the indicators of physical damage sustained by the damaged vehicle during the collision event as inference input to the trained regression machine learning model, which in response provides an output comprising a projected cost to repair the damaged vehicle and a projected cost to treat bodily injury sustained by an occupant of the damaged vehicle during the collision event, at 714.

In some embodiments, the output of the trained regression machine learning model may include a correlation indicator indicating a degree of correlation between the projected cost to repair the damaged vehicle and the projected cost to treat the bodily injury sustained by the occupant during the collision event. In some embodiments, the output of the trained regression machine learning model may include estimated ranges of cost of for vehicle repairs and medical treatments. These two costs indicators may then be further binned into different class claims like low-cost claims that have prescribed cost range (e.g., a few thousand dollars) or moderate cost claims (e.g., between a few thousand dollars and mid tens of thousands of dollars) or high-cost claims (e.g., above $20,000). The correlation between these two costs may further serve as a confidence indicator that these costs are reasonable. A low variance and correlated costs may indicate high confidence.

In some embodiments, PHI-compliant occupant metadata may be provided as part of the inference input to the trained regression machine learning model. Example occupant metadata may include an age of the occupant of the damaged vehicle, a height of the occupant of the damaged vehicle, a weight of the occupant of the damaged vehicle, a gender of the occupant of the damaged vehicle, and a role of the occupant of the damaged vehicle in operating the damaged vehicle. Other occupant metadata may be employed as well.

In some embodiments, collision metadata may be provided as part of the inference input to the trained regression machine learning model. Example collision metadata may include an indicator of the seat in which the occupant was seated in the damaged vehicle during the collision event, an indicator of seatbelt usage for the seat in which the occupant was seated in the damaged vehicle during the collision event, airbag status for the seat in which the occupant was seated in the damaged vehicle during the collision event, and a change in velocity of the damaged vehicle during the collision event. Other collision metadata may be employed as well.

In some embodiments, injury claim data representing the bodily injury claim related to the occupant of the damaged vehicle and the collision event may be provided as part of the inference input to the trained regression machine learning model.

In some embodiments, output of the trained regression machine learning model may include a mapping of locations of vehicle physical damage to locations of bodily injury, for example as described above with reference to FIG. 4.

Referring again to FIG. 7, the process 700 may include providing the PDBI cost analysis 262 of FIG. 2 to an analyst, at 716 of FIG. 7. The analyst may employ the PDBI cost analysis 262 in evaluating a bodily injury claim related to the occupant of the damaged vehicle and the collision event and a damaged vehicle physical damage claim related to the collision event The PDBI cost analysis 262 provides several advantages. By providing a projected cost to repair the damaged vehicle, the PDBI cost analysis 262 improves the adjuster's ability to analyze physical damage claims. Use of the PDBI cost analysis 262 may improve cycle time efficiency, while providing explainable, transparent, and bias free consistent decisions which are highly accurate. And by providing a projected cost to treat bodily injury sustained by an occupant of the damaged vehicle, the PDBI cost analysis 262 improves the adjuster's ability to analyze bodily injury claims.

Medical Treatment Analysis

The medical treatment analysis 264 may include a predicted frequency and/or duration of medical treatments to treat bodily injury sustained by a vehicle occupant during a vehicle collision event. An analyst may employ the medical treatment analysis 264 to evaluate bodily injury claims submitted by the occupant, for example to determine duration of medical treatment and to determine whether these claims are fraudulent.

FIG. 8 illustrates a process 800 for generating a PDBI Cost Analysis according to some embodiments of the disclosed technology. The process 800 may be executed, for example, by the adaptive analytics system 100 of FIG. 1. The elements of process 800 are presented in a particular order. However, it should be understood that, in various embodiments, one or more elements may be performed in a different order, in parallel, or omitted. Furthermore, the process 800 may include other elements in addition to those presented. For example, the process 800 may include error-handling functions if exceptions occur, and the like.

Referring to FIG. 8, the process 800 may include generating a computer vision training data set comprising historical correspondences between examples of images and attributes of damaged vehicles and corresponding examples of classes of severity of physical damage sustained by the damaged vehicles, at 802.

Referring again to FIG. 8, the process 800 may include training a computer vision machine learning model using the computer vision training data set, at 804. The computer vision machine learning model may be implemented as a convolutional neural network.

Referring again to FIG. 8, the process 800 may include generating a regression training data set comprising historical correspondences between examples of indicators of physical damage sustained by damaged vehicles during collision events and corresponding examples of frequencies and/or durations of medical treatments to treat bodily injuries sustained by occupants of the damaged vehicles during the collision event, at 806. The training data may include bodily injury claim duration to enable prediction of the length of time for a bodily injury claim. Here the regression model predicts estimated duration of medical treatment (e.g., as a number of days). Based on the cost analysis of the regression model, a high-value claim (i.e., a claim having higher costs) may indicate a greater duration of medical treatments.

Referring again to FIG. 8, the process 800 may include training a regression machine learning model using the regression training data set, at 808. The training may take the form of supervised learning, where input features and output labels are associated in the regression training data set.

In some embodiments, the computer vision machine learning model and the regression machine learning model may be implemented together as a multi-modal model. In such embodiments, the multi-modal model may be trained using both the computer vision training data set and the regression training data set.

Referring again to FIG. 8, the process 800 may include obtaining images and attributes of a damaged vehicle that has been damaged in a collision event, at 810. Example attributes of the damaged vehicle may include a vehicle identification number (VIN) of the damaged vehicle, make of the damaged vehicle, sub model of the damaged vehicle, model of the damaged vehicle, year or age of the damaged vehicle, mileage of the damaged vehicle, transmission parameters of a transmission of the damaged vehicle, and engine and/or motor parameters of an engine and/or motor of the damaged vehicle. Other attributes of the damaged vehicle may be employed as well.

Referring again to FIG. 8, the process 800 may include providing the obtained images and attributes of the damaged vehicle as inference input to the trained computer vision machine learning model, which in response provides a first output comprising a predicted class of severity of the physical damage sustained by the damaged vehicle during the collision event, at 812. The predicted class of severity may be one of multiple possible predicted classes of severity. Each of the multiple possible predicted classes of severity may indicate a respective severity of physical damage sustained by the damaged vehicle during the collision event.

In some embodiments, the predicted class of severity indicates a type of the physical damage sustained by the damaged vehicle during the collision event. In some embodiments, the predicted class of severity indicates whether the damage sustained by the damaged vehicle during the collision event represents a partial loss of the damaged vehicle or a total loss of the damaged vehicle.

Referring again to FIG. 8, the process 800 may include providing the predicted class of severity of physical damage sustained by the damaged vehicle during the collision event as inference input to the trained regression machine learning model, which in response provides a second output comprising a predicted frequency and/or duration of medical treatments to treat bodily injury sustained by an occupant of the damaged vehicle during the collision event, at 814. In some embodiments, the duration may be inferred based on historical claims. In some embodiments, a third-party resource and/or a National collision/injury treatment database may also facilitate determination of typical medical treatment durations for common vehicle collision damage.

In some embodiments, the output of the trained regression machine learning model may include a correlation indicator indicating a degree of correlation between the projected cost to repair the damaged vehicle and the projected cost to treat the bodily injury sustained by the occupant during the collision event. In some embodiments, the output of the trained regression machine learning model may include estimated ranges of cost of for vehicle repairs and medical treatments. These two costs indicators may then be further binned into different class claims like low-cost claims that have prescribed cost range (e.g., a few thousand dollars) or moderate cost claims (e.g., between a few thousand dollars and mid tens of thousands of dollars) or high-cost claims (e.g., above $20,000). The correlation between these two costs may further serve as a confidence indicator that these costs are reasonable. A low variance and correlated costs may indicate high confidence.

In some embodiments, occupant metadata may be provided as part of the inference input to the trained regression machine learning model. Example occupant metadata may include an age of the occupant of the damaged vehicle, a height of the occupant of the damaged vehicle, a weight of the occupant of the damaged vehicle, a gender of the occupant of the damaged vehicle, and a role of the occupant of the damaged vehicle in operating the damaged vehicle. Other occupant metadata may be employed as well.

In some embodiments, collision metadata may be provided as part of the inference input to the trained regression machine learning model. Example collision metadata may include an indicator of the seat in which the occupant was seated in the damaged vehicle during the collision event, an indicator of seatbelt usage for the seat in which the occupant was seated in the damaged vehicle during the collision event, airbag status for the seat in which the occupant was seated in the damaged vehicle during the collision event, and a change in velocity of the damaged vehicle during the collision event. Other collision metadata may be employed as well.

In some embodiments, damaged vehicle physical damage claim data related to the damaged vehicle and the collision event may be provided as part of the inference input to the trained regression machine learning model. In some embodiments, injury claim data representing the bodily injury claim related to the occupant of the damaged vehicle and the collision event may be provided as part of the inference input to the trained regression machine learning model. The injury claim data may include the duration of the claim (e.g., from claim origination to claim closure).

In some embodiments, output of the trained regression machine learning model may include a predicted type of the medical treatments. The types of the medical treatments may include surgery, medication, physical therapy, and the like.

In some embodiments, output of the trained regression machine learning model may include a mapping of locations of vehicle physical damage to locations of bodily injury, for example as described above with reference to FIG. 4.

Referring again to FIG. 8, the process 800 may include providing the medical treatment analysis 264 to an analyst, at 816. The analyst may employ the medical treatment analysis 264 in evaluating a bodily injury claim related to the occupant of the damaged vehicle and the collision event and a damaged vehicle physical damage claim related to the collision event. The medical treatment analysis 264 may include any or all of the outputs of the trained regression machine learning model.

The medical treatment analysis 264 provides several advantages. By providing a predicted frequency and/or duration of medical treatments, the medical treatment analysis 264 improves the adjuster's ability to analyze claims. Use of the medical treatment analysis 264 may improve cycle time efficiency, while providing explainable, transparent, and bias free consistent decisions which are highly accurate. Mapping locations of vehicle physical damage to locations of bodily injury also improves the adjuster's ability to analyze claims.

Legal Analysis

The legal analysis 266 may include a prediction of the likelihood of attorney representation of an occupant of a vehicle concerning a bodily injury related to a vehicle accident involving the vehicle. The legal analysis 266 may also include a classification of the injury by severity. An analyst may employ the predicted likelihood of attorney representation to evaluate an injury claimed by the occupant, for example to determine whether the claim will involve attorney representation. In some embodiments, the legal analysis 266 may be invoked when the claim has been flagged as fraudulent or an outlier.

FIGS. 9A,B illustrate a process 900 for generating a legal analysis according to some embodiments of the disclosed technology. The process 900 may be executed, for example, by the adaptive analytics system 100 of FIG. 1. The elements of process 900 are presented in a particular order. However, it should be understood that, in various embodiments, one or more elements may be performed in a different order, in parallel, or omitted. Furthermore, the process 900 may include other elements in addition to those presented. For example, the process 900 may include error-handling functions if exceptions occur, and the like.

Referring to FIG. 9A, the process 900 may include generating a computer vision training data set comprising historical correspondences between examples of images and attributes of damaged vehicles and corresponding examples of indicators of physical damage sustained by the damaged vehicles, at 902.

Referring again to FIG. 9A, the process 900 may include training a computer vision machine learning model using the computer vision training data set, at 904. The computer vision machine learning model may be implemented as a convolutional neural network.

Referring again to FIG. 9A, the process 900 may include generating a classifier training data set (also referred to herein as the "bodily injury classifier training data set") comprising historical correspondences between examples of indicators of physical damage sustained by damaged vehicles during collision events and corresponding examples of classes of bodily injury sustained by occupants of the damaged vehicles during the collision events, at 906.

Referring again to FIG. 9A, the process 900 may include training a classifier machine learning model (also referred to herein as the "bodily injury classifier machine learning model") using the bodily injury classifier training data set, at 908. The training of the bodily injury classifier machine learning model may include mapping physical damage estimates to bodily injury claims. The training of the bodily injury classifier machine learning model may include applying labels for injury potential to classes of bodily injury given physical damage patterns.

In some embodiments, the computer vision machine learning model and the bodily injury classifier machine learning model may be implemented together as a multi-modal model. In such embodiments, the multi-modal model may be trained using both the computer vision training data set and the bodily injury classifier training data set.

Referring again to FIG. 9A, the process 900 may include obtaining images and attributes of a damaged vehicle that has been damaged in a collision event, at 910. Example attributes of the damaged vehicle may include a vehicle identification number (VIN) of the damaged vehicle, make of the damaged vehicle, sub model of the damaged vehicle, model of the damaged vehicle, year or age of the damaged vehicle, mileage of the damaged vehicle, transmission parameters of a transmission of the damaged vehicle, and engine and/or motor parameters of an engine and/or motor of the damaged vehicle. Other attributes of the damaged vehicle may be employed as well.

Referring again to FIG. 9A, the process 900 may include providing the obtained images and attributes of the damaged vehicle as inference input to the trained computer vision machine learning model, which in response provides a first output comprising indicators of physical damage sustained by the damaged vehicle during the collision event, at 912. Example indicators of physical damage sustained by the damaged vehicle during the collision event may include a point of impact that indicates a location where the damaged vehicle collided with a physical object during the collision event, a type of the physical damage sustained by the damaged vehicle during the collision event, a repair cost estimate of a cost of repairing the damage sustained by the damaged vehicle during the collision event, a loss flag indicating whether the damage sustained by the damaged vehicle during the collision event represents a partial loss of the damaged vehicle or a total loss of the damaged vehicle, a fluid flag indicating whether fluid leaked from the damaged vehicle during the collision event, a glass flag indicating whether glass of the damaged vehicle was damaged during the collision event, an airbag flag indicating whether an airbag of the damaged vehicle deployed during the collision event, and a drivable flag indicating whether the damaged vehicle was drivable after the collision event. Other indicators of physical damage sustained by the damaged vehicle during the collision event may be employed as well.

Referring again to FIG. 9A, the process 900 may include providing the indicators of physical damage sustained by the damaged vehicle during the collision event as inference input to the trained bodily injury classifier machine learning model, which in response provides a second output comprising a predicted class of bodily injury sustained by an occupant of the damaged vehicle during the collision event and a confidence indicator representing a level of confidence that the predicted class of bodily injury is correct, at 914. The predicted class of bodily injury may be one of multiple possible predicted classes of bodily injury. Each of the multiple possible predicted classes of bodily injury may indicate a respective severity of bodily injury. Example classes of bodily injury may include a no injury class indicating no bodily injury, a moderate injury class indicating moderate bodily injury, and a severe injury class indicating severe bodily injury. Other classes of bodily injury may be employed as well.

In some embodiments, the indicators of physical damage sustained by the damaged vehicle during the collision event include a physical damage severity class indicating a severity of the physical damage. In such embodiments, the output of the trained classifier machine learning model may include a correlation indicator indicating a degree of correlation between the predicted class of bodily injury and the physical damage severity class.

In some embodiments, occupant metadata may be provided as part of the inference input to the trained bodily injury classifier machine learning model. Example occupant metadata may include an age of the occupant of the damaged vehicle, a height of the occupant of the damaged vehicle, a weight of the occupant of the damaged vehicle, a gender of the occupant of the damaged vehicle, and a role of the occupant of the damaged vehicle in operating the damaged vehicle. Other occupant metadata may be employed as well.

In some embodiments, collision metadata may be provided as part of the inference input to the trained bodily injury classifier machine learning model. Example collision metadata may include an indicator of the seat in which the occupant was seated in the damaged vehicle during the collision event, an indicator of seatbelt usage for the seat in which the occupant was seated in the damaged vehicle during the collision event, airbag status for the seat in which the occupant was seated in the damaged vehicle during the collision event, and a change in velocity of the damaged vehicle during the collision event. Other collision metadata may be employed as well.

In some embodiments, injury claim data representing the bodily injury claim related to the occupant of the damaged vehicle and the collision event may be provided as part of the inference input to the trained bodily injury classifier machine learning model.

In some embodiments, output of the trained bodily injury classifier machine learning model may include a mapping of locations of vehicle physical damage to locations of bodily injury, for example as described above with reference to FIG. 4.

The process 900 may include determining a likelihood of attorney representation of the occupant concerning the bodily injury based on the predicted class of bodily injury sustained by the occupant. In some embodiments, this determination may be made using rules, settings, mappings, and the like. For example, a mapping may map each class of bodily injury to a respective likelihood of attorney representation. In some embodiments, this determination may be made using an additional classifier machine learning model, for example as described below.

Referring now to FIG. 9B, the process 900 may include generating a classifier training data set (also referred to herein as the "legal classifier training data set") comprising historical correspondences between examples of classes of bodily injury sustained by occupants of damaged vehicles during collision events and corresponding examples of whether the occupants were subsequently represented by attorneys concerning the bodily injuries, at 916.

Referring again to FIG. 9B, the process 900 may include training a classifier machine learning model (also referred to herein as the "legal classifier machine learning model") using the legal classifier training data set, at 918.

In some embodiments, any two or three of the computer vision machine learning models, the bodily injury classifier machine learning model, and the legal classifier machine learning model may be implemented together as a multi-modal model. In such embodiments, the multi-modal model may be trained using the corresponding training data sets.

Referring again to FIG. 9B, the process 900 may include providing the predicted class of bodily injury sustained by the occupant as inference input to the trained legal classifier machine learning model, wherein responsive to the inference input, the trained legal classifier machine learning model provides an output comprising a likelihood of attorney representation of the occupant concerning the bodily injury, at 920.

Referring again to FIG. 9B, the process 900 may include providing the legal analysis 266 to an analyst, at 922. The legal analyst may employ the legal analysis 266 in evaluating a bodily injury claim related to the occupant of the damaged vehicle and the collision event. The legal analysis 266 may include any or all of the outputs of the trained legal classifier machine learning model and the trained bodily injury machine learning model. In some embodiments, the legal analysis 266 may include the predicted class of bodily injury and the confidence indicator.

In some embodiments, the legal analysis 266 of FIG. 2 may include a probabilistic score of injury severity. In some embodiments, the legal analysis 266 may include a probabilistic score relating injury likelihood to partial loss or total loss of the vehicle. In some embodiments, the legal analysis 266 may include a mapping of locations of vehicle physical damage to locations of bodily injury, for example as described above with reference to FIG. 4. In some embodiments, the legal analysis 266 may include the vehicle physical damage photos, which may be organized according to the severity of the damage depicted.

The legal analysis 266 provides several advantages. By providing a likelihood of attorney representation, the legal analysis 266 improves the adjuster's ability to negotiate with an attorney representing the vehicle occupant claiming bodily injury. Use of the legal analysis 266 may improve cycle time efficiency, while providing explainable, transparent, and bias free consistent decisions which are highly accurate. Mapping locations of vehicle physical damage to locations of bodily injury also improves the adjuster's ability to analyze claims. Organizing the vehicle damage photos in one place and by damage severity reduces the amount of time needed by the adjuster to analyze the physical damage and bodily injury claims. Mapping locations of vehicle physical damage to locations of bodily injury also improves the adjuster's ability to analyze claims.

Machine Learning Models

Various embodiments may employ various machine learning models at one or more points in the described processes. For example, the machine learning models and techniques may include classifiers, decision trees, neural networks, gradient boosting, generative language models, regression models, and similar machine learning models and techniques.

For example, a deep neural network (DNN) may have multiple hidden layers of units between an input and output. For example, the DNN may include multiple hidden layers between the input and output layer, and may use multiple processing layers composed of multiple linear and/or non-linear transformations. Additionally, the DNN may have a structure, and synaptic weights trained using semi-supervised machine learning techniques in conjunction with labelled and unlabeled data to encode knowledge obtained from historic data.

The neural network may include a feature extraction layer that extracts feature from the input data. In some embodiments, this process may be performed after input data preprocessing. The preprocessing may include input data transformation. The input data transformation may include converting different file types (e.g., image and/or video stream format, word format, etc.) into a unified digital format (e.g., pdf file). The preprocessing may include data extraction. The data extraction may include extracting useful information, for example using optical character recognition (OCR) and natural language processing (NLP) techniques.

The feature extraction in the feature extraction layer may be performed against the extracted data. For example, the features for extraction may include identifiers of damaged parts identified in the images of the damaged vehicles. The selection of the features for extraction may also be determined by learning importance scores for the candidate features using a tree-based machine learning model.

Tree-based machine learning models for feature selection may use Random Forests or Gradient Boosting. The model includes an ensemble of decision trees that collectively make predictions. To begin, the tree-based model may be trained on a labeled dataset. The dataset may include historical images of damaged vehicles and/or historical vehicle repair estimate data structures, along with corresponding output vehicle repair estimate data structures.

As the tree-based machine learning model learns to make predictions, it recursively splits the data based on different features, constructing a tree structure that captures patterns in the data. The goal of the training is to make the predictions as close to the ground truth labels as possible. One of the advantages of tree-based models is that they can generate feature importance scores for each input feature. These scores reflect the relative importance of each feature in contributing to the model's predictive power. A higher importance score indicates that a feature has a greater influence on the model's decision-making process.

In some embodiments, Gini importance metrics may be used for feature importance in the tree-based model. Gini importance quantifies the total reduction in the Gini impurity achieved by each feature across all the trees in the ensemble. Features that lead to a substantial decrease in impurity when used for splitting the data are assigned higher importance scores.

Once the tree-based model is trained, the feature importance scores may be extracted. By sorting the features in descending order based on their scores, a ranked list of features may be obtained. This ranking enables prioritizing the features that have the most impact on the model's decision-making process.

Based on the feature ranking, the top features may be extracted from incoming images of damaged vehicles and fed into the neural network to output the described data structures.

The neural network may include an output layer that provides output data based on the input data. For example, the output layer of a classifier may use a sigmoid activation function that outputs a probability value between 0 and 1 for each class.

During inference operation, electronic records may be provided as inference input data to a trained machine learning model. An input layer of the model may extract one or more parameters as input data from the electronic records. Responsive to the inference input, an output layer of the model may provide output representing a selection probability for each electronic vehicle diagnostic record.

Some embodiments include the training of the machine learning models. The training may be supervised, unsupervised, or a combination thereof, and may continue between operations for the lifetime of the system. The training may include creating a training set that includes the input parameters and corresponding assessments described above.

The training may include one or more second stages. A second stage may follow the training and use of the trained machine learning models, and may include creating a second training set, and training the trained machine learning models using the second training set. The second training set may include the inputs applied to the machine learning models, and the corresponding outputs generated by the machine learning models, during actual use of the machine learning models.

The second training stage may include identifying erroneous assessments generated by the machine learning model, and adding the identified erroneous assessments to the second training set. Creating the second training set may also include adding the inputs corresponding to the identified erroneous assessments to the second training set.

Different iterations may employ the same trained machine learning model and/or different trained machine learning models. For example, a first iteration may employ a cosine similarity or machine model. A second iteration may employ an auto encoder, STOSA, or machine model. A third iteration may employ a group NN or machine model. Subsequent iterations may employ a STOSA or machine model.

Computing Environment

Figure 10:
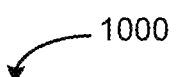
FIG. 10 is an example computing component that may be used to implement various features of embodiments described in the present disclosure.

FIG. 10 depicts a block diagram of an example computer system 1000 in which embodiments described herein may be implemented. The computer system 1000 includes a bus 1002 or other communication mechanism for communicating information, one or more hardware processors 1004 coupled with bus 1002 for processing information. Hardware processor(s) 1004 may be, for example, one or more microprocessors.

The computer system 1000 also includes a main memory 1006, such as a random-access memory (RAM), cache and/or other dynamic storage devices, coupled to bus 1002 for storing information and instructions to be executed by processor 1004. Main memory 1006 also may be used for storing temporary variables or other intermediate information during execution of instructions to be executed by processor 1004. Such instructions, when stored in storage media accessible to processor 1004, render computer system 1000 into a special-purpose machine that is customized to perform the operations specified in the instructions.

The computer system 1000 further includes a read only memory (ROM) 1008 or other static storage device coupled to bus 1002 for storing static information and instructions for processor 1004. A storage device 1010, such as a magnetic disk, optical disk, or USB thumb drive (Flash drive), etc., is provided and coupled to bus 1002 for storing information and instructions.

The computer system 1000 may be coupled via bus 1002 to a display 1012, such as a liquid crystal display (LCD) (or touch screen), for displaying information to a computer user. An input device 1014, including alphanumeric and other keys, is coupled to bus 1002 for communicating information and command selections to processor 1004. Another type of user input device is cursor control 1016, such as a mouse, a trackball, or cursor direction keys for communicating direction information and command selections to processor 1004 and for controlling cursor movement on display 1012. In some embodiments, the same direction information and command selections as cursor control may be implemented via receiving touches on a touch screen without a cursor.

The computing system 1000 may include a user interface module to implement a GUI that may be stored in a mass storage device as executable software codes that are executed by the computing device(s). This and other modules may include, by way of example, components, such as software components, object-oriented software components, class components and task components, processes, functions, attributes, procedures, subroutines, segments of program code, drivers, firmware, microcode, circuitry, data, databases, data structures, tables, arrays, and variables.

In general, the word "component," "engine," "system," "database," data store," and the like, as used herein, can refer to logic embodied in hardware or firmware, or to a collection of software instructions, possibly having entry and exit points, written in a programming language, such as, for example, Java, C, C++, and Python. A software component may be compiled and linked into an executable program, installed in a dynamic link library, or may be written in an interpreted programming language such as, for example, BASIC, Perl, or Python. It will be appreciated that software components may be callable from other components or from themselves, and/or may be invoked in response to detected events or interrupts. Software components configured for execution on computing devices may be provided on a computer readable medium, such as a compact disc, digital video disc, flash drive, magnetic disc, or any other tangible medium, or as a digital download (and may be originally stored in a compressed or installable format that requires installation, decompression or decryption prior to execution). Such software code may be stored, partially or fully, on a memory device of the executing computing device, for execution by the computing device. Software instructions may be embedded in firmware, such as an EPROM. It will be further appreciated that hardware components may be comprised of connected logic units, such as gates and flip-flops, and/or may be comprised of programmable units, such as programmable gate arrays or processors.

The computer system 1000 may implement the techniques described herein using customized hard-wired logic, one or more ASICs or FPGAs, firmware and/or program logic which in combination with the computer system causes or programs computer system 1000 to be a special-purpose machine. According to one embodiment, the techniques herein are performed by computer system 1000 in response to processor(s) 1004 executing one or more sequences of one or more instructions contained in main memory 1006. Such instructions may be read into main memory 1006 from another storage medium, such as storage device 1010. Execution of the sequences of instructions contained in main memory 1006 causes processor(s) 1004 to perform the process steps described herein. In alternative embodiments, hard-wired circuitry may be used in place of or in combination with software instructions.

The term "non-transitory media," and similar terms, as used herein refers to any media that store data and/or instructions that cause a machine to operate in a specific fashion. Such non-transitory media may comprise non-volatile media and/or volatile media. Non-volatile media includes, for example, optical or magnetic disks, such as storage device 1010. Volatile media includes dynamic memory, such as main memory 1006. Common forms of non-transitory media include, for example, a floppy disk, a flexible disk, hard disk, solid state drive, magnetic tape, or any other magnetic data storage medium, a CD-ROM, any other optical data storage medium, any physical medium with patterns of holes, a RAM, a PROM, and EPROM, a FLASH-EPROM, NVRAM, any other memory chip or cartridge, and networked versions of the same.

Non-transitory media is distinct from but may be used in conjunction with transmission media. Transmission media participates in transferring information between non-transitory media. For example, transmission media includes coaxial cables, copper wire and fiber optics, including the wires that comprise bus 1002. Transmission media can also take the form of acoustic or light waves, such as those generated during radio-wave and infra-red data communications.

The computer system 1000 also includes a communication interface 1018 coupled to bus 1002. Network interface 1018 provides a two-way data communication coupling to one or more network links that are connected to one or more local networks. For example, communication interface 1018 may be an integrated services digital network (ISDN) card, cable modem, satellite modem, or a modem to provide a data communication connection to a corresponding type of telephone line. As another example, network interface 1018 may be a local area network (LAN) card to provide a data communication connection to a compatible LAN (or a WAN component to communicate with a WAN). Wireless links may also be implemented. In any such implementation, network interface 1018 sends and receives electrical, electromagnetic or optical signals that carry digital data streams representing various types of information.

A network link typically provides data communication through one or more networks to other data devices. For example, a network link may provide a connection through local network to a host computer or to data equipment operated by an Internet Service Provider (ISP). The ISP in turn provides data communication services through the worldwide packet data communication network now commonly referred to as the "Internet." Local network and Internet both use electrical, electromagnetic or optical signals that carry digital data streams. The signals through the various networks and the signals on network link and through communication interface 1018, which carry the digital data to and from computer system 1000, are example forms of transmission media.

The computer system 1000 can send messages and receive data, including program code, through the network(s), network link and communication interface 1018. In the Internet example, a server might transmit a requested code for an application program through the Internet, the ISP, the local network and the communication interface 1018.

The received code may be executed by processor 1004 as it is received, and/or stored in storage device 1010, or other non-volatile storage for later execution.

Each of the processes, methods, and algorithms described in the preceding sections may be embodied in, and fully or partially automated by, code components executed by one or more computer systems or computer processors comprising computer hardware. The one or more computer systems or computer processors may also operate to support performance of the relevant operations in a "cloud computing" environment or as a "software as a service" (SaaS). The processes and algorithms may be implemented partially or wholly in application-specific circuitry. The various features and processes described above may be used independently of one another, or may be combined in various ways. Different combinations and sub-combinations are intended to fall within the scope of this disclosure, and certain method or process blocks may be omitted in some implementations. The methods and processes described herein are also not limited to any particular sequence, and the blocks or states relating thereto can be performed in other sequences that are appropriate, or may be performed in parallel, or in some other manner. Blocks or states may be added to or removed from the disclosed example embodiments. The performance of certain of the operations or processes may be distributed among computer systems or computers processors, not only residing within a single machine, but deployed across a number of machines.

As used herein, a circuit might be implemented utilizing any form of hardware, or a combination of hardware and software. For example, one or more processors, controllers, ASICs, PLAs, PALs, CPLDs, FPGAs, logical components, software routines or other mechanisms might be implemented to make up a circuit. In implementation, the various circuits described herein might be implemented as discrete circuits or the functions and features described can be shared in part or in total among one or more circuits. Even though various features or elements of functionality may be individually described or claimed as separate circuits, these features and functionality can be shared among one or more common circuits, and such description shall not require or imply that separate circuits are required to implement such features or functionality. Where a circuit is implemented in whole or in part using software, such software can be implemented to operate with a computing or processing system capable of carrying out the functionality described with respect thereto, such as computer system 1000.

As used herein, the term "or" may be construed in either an inclusive or exclusive sense. Moreover, the description of resources, operations, or structures in the singular shall not be read to exclude the plural. Conditional language, such as, among others, "can," "could," "might," or "may," unless specifically stated otherwise, or otherwise understood within the context as used, is generally intended to convey that certain embodiments include, while other embodiments do not include, certain features, elements and/or steps.

Terms and phrases used in this document, and variations thereof, unless otherwise expressly stated, should be construed as open ended as opposed to limiting. Adjectives such as "conventional," "traditional," "normal," "standard," "known," and terms of similar meaning should not be construed as limiting the item described to a given time period or to an item available as of a given time, but instead should be read to encompass conventional, traditional, normal, or standard technologies that may be available or known now or at any time in the future. The presence of broadening words and phrases such as "one or more," "at least," "but not limited to" or other like phrases in some instances shall not be read to mean that the narrower case is intended or required in instances where such broadening phrases may be absent.

What is claimed is:

1. A system, comprising:

one or more hardware processors; and one or more non-transitory machine-readable storage media encoded with instructions that, when executed by the one or more hardware processors, cause the system to perform operations comprising:

obtaining images and attributes of a damaged vehicle that has been damaged in a collision event;

providing the obtained images and attributes of the damaged vehicle as first inference input to a trained computer vision machine learning model, wherein responsive to the first inference input, the computer vision machine learning model provides a first output comprising indicators of physical damage sustained by the damaged vehicle during the collision event, wherein the trained computer vision machine learning model has been trained with first training data comprising historical correspondences between examples of the first inference input and corresponding examples of the first output;

providing the indicators of physical damage sustained by the damaged vehicle during the collision event as second inference input to a trained classifier machine learning model, wherein responsive to the second inference input, the trained classifier machine learning model provides a second output comprising a predicted likelihood that bodily injury was sustained by an occupant of the damaged vehicle during the collision event and a confidence indicator representing a level of confidence that the predicted likelihood that bodily injury was sustained is correct, wherein the predicted likelihood that bodily injury was sustained is one of multiple possible likelihoods of bodily injury, wherein each of the multiple likelihoods of bodily injury indicates a respective likelihood of bodily injury, and wherein the trained classifier machine learning model has been trained with second training data comprising historical correspondences between examples of the second inference input and corresponding examples of the second output; and providing the predicted likelihood of bodily injury and the confidence indicator to an analyst for use in evaluating a bodily injury claim related to the occupant of the damaged vehicle and the collision event.

2. The system of claim 1, wherein the indicators of physical damage sustained by the damaged vehicle during the collision event comprise at least one of:

a point of impact that indicates a location where the damaged vehicle collided with a physical object during the collision event;

a type of the physical damage sustained by the damaged vehicle during the collision event;

a repair cost estimate of a cost of repairing the damage sustained by the damaged vehicle during the collision event;

a loss flag indicating whether the damage sustained by the damaged vehicle during the collision event represents a partial loss of the damaged vehicle or a total loss of the damaged vehicle;

a fluid flag indicating whether fluid leaked from the damaged vehicle during the collision event;

a glass flag indicating whether glass of the damaged vehicle was damaged during the collision event;

an airbag flag indicating whether an airbag of the damaged vehicle deployed during the collision event; and a drivable flag indicating whether the damaged vehicle was drivable after the collision event.

3. The system of claim 1, wherein the attributes of the damaged vehicle comprise at least one of:

a vehicle identification number (VIN) of the damaged vehicle;

make of the damaged vehicle;

submodel of the damaged vehicle;

model of the damaged vehicle;

year or age of the damaged vehicle;

mileage of the damaged vehicle;

transmission parameters of a transmission of the damaged vehicle; and engine and/or motor parameters of an engine and/or motor of the damaged vehicle.

4. The system of claim 1, wherein the multiple possible predicted likelihoods of bodily injury comprise:

a likely predicted likelihood indicating bodily injury is likely;

an unlikely predicted likelihood indicating bodily injury is unlikely; and an uncertain predicted likelihood indicating bodily injury is uncertain.

5. The system of claim 1, the operations further comprising:

providing occupant metadata as part of the second inference input to the trained classifier machine learning model, wherein the occupant metadata comprises at least one of:

an age of the occupant of the damaged vehicle;

a height of the occupant of the damaged vehicle;

a weight of the occupant of the damaged vehicle; and a role of the occupant of the damaged vehicle in operating the damaged vehicle.

6. The system of claim 1, the operations further comprising:

providing collision metadata as part of the second inference input to the trained classifier machine learning model, wherein the collision metadata comprises at least one of:

an indicator of the seat in which the occupant was seated in the damaged vehicle during the collision event;

an indicator of seatbelt usage for the seat in which the occupant was seated in the damaged vehicle during the collision event;

airbag status for the seat in which the occupant was seated in the damaged vehicle during the collision event; and a change in velocity of the damaged vehicle during the collision event.

7. The system of claim 1, the operations further comprising:

providing injury claim data representing the bodily injury claim related to the occupant of the damaged vehicle and the collision event as part of the second inference input to the trained classifier machine learning model.

8. One or more non-transitory machine-readable storage media encoded with instructions that, when executed by one or more hardware processors of a computing system, cause the computing system to perform operations comprising:

obtaining images and attributes of a damaged vehicle that has been damaged in a collision event;

providing the obtained images and attributes of the damaged vehicle as first inference input to a trained computer vision machine learning model, wherein responsive to the first inference input, the computer vision machine learning model provides a first output comprising indicators of physical damage sustained by the damaged vehicle during the collision event, wherein the trained computer vision machine learning model has been trained with first training data comprising historical correspondences between examples of the first inference input and corresponding examples of the first output;

providing the indicators of physical damage sustained by the damaged vehicle during the collision event as second inference input to a trained classifier machine learning model, wherein responsive to the second inference input, the trained classifier machine learning model provides a second output comprising a predicted likelihood that bodily injury was sustained by an occupant of the damaged vehicle during the collision event and a confidence indicator representing a level of confidence that the predicted likelihood that bodily injury was sustained is correct, wherein the predicted likelihood that bodily injury was sustained is one of multiple possible likelihoods of bodily injury, wherein each of the multiple likelihoods of bodily injury indicates a respective likelihood of bodily injury, and wherein the trained classifier machine learning model has been trained with second training data comprising historical correspondences between examples of the second inference input and corresponding examples of the second output; and providing the predicted likelihood of bodily injury and the confidence indicator to an analyst for use in evaluating a bodily injury claim related to the occupant of the damaged vehicle and the collision event.

9. The one or more non-transitory machine-readable storage media of claim 8, wherein the indicators of physical damage sustained by the damaged vehicle during the collision event comprise at least one of:

a point of impact that indicates a location where the damaged vehicle collided with a physical object during the collision event;

a type of the physical damage sustained by the damaged vehicle during the collision event;

a repair cost estimate of a cost of repairing the damage sustained by the damaged vehicle during the collision event;

a loss flag indicating whether the damage sustained by the damaged vehicle during the collision event represents a partial loss of the damaged vehicle or a total loss of the damaged vehicle;

a fluid flag indicating whether fluid leaked from the damaged vehicle during the collision event;

a glass flag indicating whether glass of the damaged vehicle was damaged during the collision event;

an airbag flag indicating whether an airbag of the damaged vehicle deployed during the collision event; and a drivable flag indicating whether the damaged vehicle was drivable after the collision event.

10. The one or more non-transitory machine-readable storage media of claim 8, wherein the attributes of the damaged vehicle comprise at least one of:

a vehicle identification number (VIN) of the damaged vehicle;

make of the damaged vehicle;

submodel of the damaged vehicle;

model of the damaged vehicle;

year or age of the damaged vehicle;

mileage of the damaged vehicle;

transmission parameters of a transmission of the damaged vehicle; and engine and/or motor parameters of an engine and/or motor of the damaged vehicle.

11. The one or more non-transitory machine-readable storage media of claim 8, wherein the multiple possible predicted likelihoods of bodily injury comprise:

a likely predicted likelihood indicating bodily injury is likely;

an unlikely predicted likelihood indicating bodily injury is unlikely; and an uncertain predicted likelihood indicating bodily injury is uncertain.

12. The one or more non-transitory machine-readable storage media of claim 8, the operations further comprising:

providing occupant metadata as part of the second inference input to the trained classifier machine learning model, wherein the occupant metadata comprises at least one of:

an age of the occupant of the damaged vehicle;

a height of the occupant of the damaged vehicle;

a weight of the occupant of the damaged vehicle; and a role of the occupant of the damaged vehicle in operating the damaged vehicle.

13. The one or more non-transitory machine-readable storage media of claim 8, the operations further comprising:

providing collision metadata as part of the second inference input to the trained classifier machine learning model, wherein the collision metadata comprises at least one of:
an indicator of the seat in which the occupant was seated in the damaged vehicle during the collision event;
an indicator of seatbelt usage for the seat in which the occupant was seated in the damaged vehicle during the collision event;
airbag status for the seat in which the occupant was seated in the damaged vehicle during the collision event; and
a change in velocity of the damaged vehicle during the collision event.

14. The one or more non-transitory machine-readable storage media of claim 8, the operations further comprising:
providing injury claim data representing the bodily injury claim related to the occupant of the damaged vehicle and the collision event as part of the second inference input to the trained classifier machine learning model.

15. A computer-implemented method comprising:
obtaining images and attributes of a damaged vehicle that has been damaged in a collision event;
providing the obtained images and attributes of the damaged vehicle as first inference input to a trained computer vision machine learning model, wherein responsive to the first inference input, the computer vision machine learning model provides a first output comprising indicators of physical damage sustained by the damaged vehicle during the collision event, wherein the trained computer vision machine learning model has been trained with first training data comprising historical correspondences between examples of the first inference input and corresponding examples of the first output;
providing the indicators of physical damage sustained by the damaged vehicle during the collision event as second inference input to a trained classifier machine learning model, wherein responsive to the second inference input, the trained classifier machine learning model provides a second output comprising a predicted likelihood that bodily injury was sustained by an occupant of the damaged vehicle during the collision event and a confidence indicator representing a level of confidence that the predicted likelihood that bodily injury was sustained is correct, wherein the predicted likelihood that bodily injury was sustained is one of multiple possible likelihoods of bodily injury, wherein each of the multiple likelihoods of bodily injury indicates a respective likelihood of bodily injury, and wherein the trained classifier machine learning model has been trained with second training data comprising historical correspondences between examples of the second inference input and corresponding examples of the second output; and
providing the predicted likelihood of bodily injury and the confidence indicator to an analyst for use in evaluating a bodily injury claim related to the occupant of the damaged vehicle and the collision event.

16. The computer-implemented method of claim 15, wherein the indicators of physical damage sustained by the damaged vehicle during the collision event comprise at least one of:
a point of impact that indicates a location where the damaged vehicle collided with a physical object during the collision event;
a type of the physical damage sustained by the damaged vehicle during the collision event;

a repair cost estimate of a cost of repairing the damage sustained by the damaged vehicle during the collision event;
a loss flag indicating whether the damage sustained by the damaged vehicle during the collision event represents a partial loss of the damaged vehicle or a total loss of the damaged vehicle;
a fluid flag indicating whether fluid leaked from the damaged vehicle during the collision event;
a glass flag indicating whether glass of the damaged vehicle was damaged during the collision event;
an airbag flag indicating whether an airbag of the damaged vehicle deployed during the collision event; and
a drivable flag indicating whether the damaged vehicle was drivable after the collision event.

17. The computer-implemented method of claim 15, wherein the attributes of the damaged vehicle comprise at least one of:
a vehicle identification number (VIN) of the damaged vehicle;
make of the damaged vehicle;
submodel of the damaged vehicle;
model of the damaged vehicle;
year or age of the damaged vehicle;
mileage of the damaged vehicle;
transmission parameters of a transmission of the damaged vehicle; and
engine and/or motor parameters of an engine and/or motor of the damaged vehicle.

18. The computer-implemented method of claim 15, wherein the multiple possible predicted likelihoods of bodily injury comprise:
a likely predicted likelihood indicating bodily injury is likely;
an unlikely predicted likelihood indicating bodily injury is unlikely; and
an uncertain predicted likelihood indicating bodily injury is uncertain.

19. The computer-implemented method of claim 15, further comprising:
providing occupant metadata as part of the second inference input to the trained classifier machine learning model, wherein the occupant metadata comprises at least one of:
an age of the occupant of the damaged vehicle;
a height of the occupant of the damaged vehicle;
a weight of the occupant of the damaged vehicle; and
a role of the occupant of the damaged vehicle in operating the damaged vehicle.

20. The computer-implemented method of claim 15, further comprising:
providing collision metadata as part of the second inference input to the trained classifier machine learning model, wherein the collision metadata comprises at least one of:
an indicator of the seat in which the occupant was seated in the damaged vehicle during the collision event;
an indicator of seatbelt usage for the seat in which the occupant was seated in the damaged vehicle during the collision event;
airbag status for the seat in which the occupant was seated in the damaged vehicle during the collision event; and
a change in velocity of the damaged vehicle during the collision event.

21. The computer-implemented method of claim 15, further comprising:

providing injury claim data representing the bodily injury claim related to the occupant of the damaged vehicle and the collision event as part of the second inference input to the trained classifier machine learning model.

* * * * *